(12) United States Patent
Lenges et al.

(10) Patent No.: US 7,166,748 B2
(45) Date of Patent: Jan. 23, 2007

(54) DURABLE COATING COMPOSITIONS CONTAINING NOVEL ASPARTIC AMINE COMPOUNDS

(75) Inventors: Christian Peter Lenges, Wilmington, DE (US); Domenic J. Barsotti, Vineland, NJ (US); Robert John Barsotti, Franklinville, NJ (US); Kalindi Dogra, Wilmington, DE (US); Helen S. M. Lu, Wallingford, PA (US); Stefan Reinartz, Wilmington, DE (US)

(73) Assignee: E.I. duPont de Nemours & Co., Wilmington, DE (US)

( * ) Notice: Subject to any disclaimer, the term of this patent is extended or adjusted under 35 U.S.C. 154(b) by 0 days.

(21) Appl. No.: 11/303,084

(22) Filed: Dec. 14, 2005

(65) Prior Publication Data

US 2006/0155149 A1   Jul. 13, 2006

Related U.S. Application Data

(60) Provisional application No. 60/636,302, filed on Dec. 15, 2004.

(51) Int. Cl.
    *C07C 215/00* (2006.01)
(52) U.S. Cl. .................................................. 564/503
(58) Field of Classification Search ................. 564/503
    See application file for complete search history.

(56) References Cited

U.S. PATENT DOCUMENTS 5,126,170 A * 6/1992 Zwiener et al. .......... 427/385.5
5,236,741 A * 8/1993 Zwiener et al. .......... 427/385.5
5,243,012 A * 9/1993 Wicks et al. .................. 528/58
5,412,056 A * 5/1995 Zwiener et al. ............... 528/73
5,516,873 A * 5/1996 Hicks et al. ................... 528/60
5,580,945 A * 12/1996 Wade et al. ................... 528/49
6,005,062 A * 12/1999 Hansen et al. ................ 528/68

* cited by examiner

*Primary Examiner*—Thurman K. Page
*Assistant Examiner*—Chukwuma Nwaonicha

(57) ABSTRACT

A coating composition comprising a binder of
  a. polyisocyanate crosslinking agent;
  b. an isocyanate-reactive component having at least one compound having the following formula (I) including isomers and mixtures of isomers thereof:

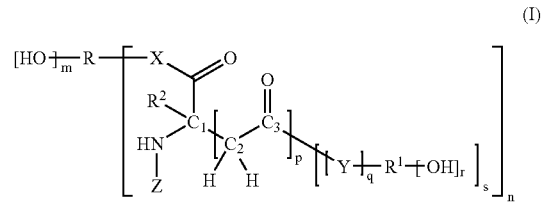

wherein
R, $R^1$, $R^2$, X, Y, Z, m, n, p, q, r and s are described in the specification and a two component composition formulated with the above constituents and substrates, such as, automotive and truck bodies and parts coated with the novel composition and novel amine and/or hydroxy amine compounds are also part of the invention.

1 Claim, No Drawings

DURABLE COATING COMPOSITIONS CONTAINING NOVEL ASPARTIC AMINE COMPOUNDS

CROSS-REFERENCE TO RELATED APPLICATION

This application claims the benefit of U.S. Provisional Application Ser. No. 60/636,302 filed on Dec. 15, 2004 which are hereby incorporated by references in its entirely.

FIELD OF THE INVENTION

This invention is directed to coating compositions, in particular, to coating compositions that are useful as exterior clear finishes for automobiles and trucks.

BACKGROUND OF THE INVENTION

The finishing system of choice presently being used on the exterior of automobiles and trucks comprises a clear coating applied over pigmented base coating that is applied over a primer coating. The clear coating provides protection, in particular, protection from weathering, to the pigmented base coating and improves the appearance of the overall finish, in particular, provides improved gloss and distinctness of image. The primer coating provides adhesion to the substrate and, in particular, provides resistance to stone chipping. When used in refinishing of automobile and truck bodies, the clear coating and primer coating are required to have an acceptable "pot life" and reasonably short cure time period to allow for application of a subsequent coat and in the case of a clear coating to allow for further processing or handling of the vehicle without damaging the finish. The term "pot life" means the period of time after a coating is mixed with a crosslinking agent, with or without a catalyst, in which the composition remains at a sprayable viscosity.

The following U.S. Pat. Nos. 5,516,873, 5,126,170, 5,243,012, 5,236,741, 5,412,056, 5,580,945, and 6,005,062, show a variety of coating composition that contain polyaspartic acid derivatives but these compositions do not have a property balance of acceptable pot life and rapid curing time to form a sufficiently hard finish to allow additional handling and processing of a coated vehicle or work piece after the coating composition has been applied.

To improve the rate of curing EP 0939091 uses reactive amine compounds. A typical example of such an amine is the reaction product of 4,4'-methylenebiscyclohexanamine with two moles of diethyl maleate. However, coating compositions formulated with these reactive amines do not have the desired balance of acceptable pot-life and the desired cure rate after application to an object while maintaining or improving on the desired properties of the resulting finish. In an effort to improve pot life, solvents and catalysts have been used but solvents have a deleterious effect on VOC (volatile organic content) emissions, which is undesirable and catalysts can result in deterioration of film properties, such as durability. It is, therefore, desired to find a class of amine functional compounds for the reaction with isocyanates, which form coating compositions that overcome these problems and form acceptable finishes for automotive and truck substrates.

The novel composition of this invention utilizes amine and hydroxy amine functional compounds that form low VOC coating compositions having an optimum balance of pot life and curing time and form finishes, in particular, clear and primer finishes useful for automobiles and trucks. The clear coatings have excellent properties, such as hardness, gloss, low color, durability, weatherability, and in particular resistance to UV (ultraviolet light) degradation, particularly when reinforced with ultraviolet light absorbers and screeners and hindered amine light stabilizers. The primer coatings exhibit excellent adhesion to metal substrates, in particular, aluminum and steel substrates, and provide for excellent stone chip resistance.

SUMMARY OF THE INVENTION

A coating composition comprising a binder of
a. polyisocyanate crosslinking agent;
b. an isocyanate-reactive component having at least one compound having the following formula (I) including isomers and mixtures of isomers thereof:

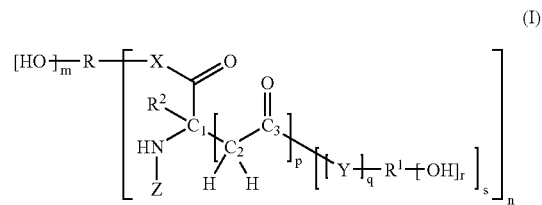

wherein
R is a hydrocarbon radical obtained by removing (m+n) hydrogen atoms from a $C_1$ to $C_{20}$ linear or branched alkyl group, or a $C_5$ to $C_{16}$ cycloaliphatic group; alternatively, R is a residue obtained by removing n amino groups from a polyether polyamine with m equal to 0 having a functionality of n and a number average molecular weight of less than 600, wherein the amino groups are attached to primary carbon atoms and the ether groups are separated by at least two carbon atoms;

m equals 0 to 4, and m preferably equals 0, 1 or 2, and n, on average, equals 1 to 4, and preferably, n, on average, equals 1 and 2, with the proviso that m cannot be 0 unless n equals at least 2 if r equals 0 and Z does not contain an OH-group, n equals 1 and r equals 1 and Z does or does not contain an OH-group, or n equals 1, r equals 0 and Z contains at least one OH-group;

X and Y each independently can be O or $NR^3$;

$R^3$ is H, or $C_1$ to $C_{20}$ linear or branched alkyl group, a $C_5$ to $C_{16}$ cycloaliphatic group, or $R^3$ is equal to $C_3$=O if s=0, i.e. the compound is a cyclic imide;

Z is selected from a $C_1$ to $C_{20}$ linear or branched alkyl group, a $C_5$ to $C_{16}$ cycloaliphatic group, or an OH-group containing linear, branched or cycloaliphatic alkyl group, preferred groups for Z are methyl, propyl, n-butyl, iso-butyl, sec-butyl, tert-butyl, or cyclohexyl; or Z comprises a fragment of the structure —$CH_2$—$CHR^4$—$R^5$, with $R^4$ equal to H, or $C_1$ to $C_{20}$ linear or branched alkyl group, or a $C_5$ to $C_{16}$ cycloaliphatic group and $R^5$ equal to —CN or —C(=O)$OR^6$, with $R^6$ equal to H, or $C_1$ to $C_{20}$ linear or branched alkyl group, or a $C_5$ to $C_{16}$ cycloaliphatic group;

p and q are equal to 0 or 1, if p and q equal to 1, the —NH-Z fragment can be bound to either $C_1$ or $C_2$, and mixtures of compounds and isomers are commonly utilized by this invention;

s is equal to 0 or 1, with the proviso that s can only be 0 if p equals 1 and X=$NR^3$ wherein $R^3$ equals $C_3$=O (cyclic imide);

$R^2$ is H or independently selected from a $C_1$ to $C_{20}$ linear or branched alkyl group, or a $C_5$ to $C_{16}$ cycloaliphatic group;

$R^1$ is a hydrocarbon radical obtained by removing (q+r) hydrogen atoms from a $C_1$ to $C_{20}$ linear or branched alkyl group, or a $C_5$ to $C_{16}$ cycloaliphatic group; and r is equal to 0 to 4, and r preferably, equal to 0 or 1.

Two component composition formulated with the above constituents, substrates, such as, automotive and truck bodies and parts coated with the novel composition and novel amine and/or hydroxy amine compounds are also part of this invention.

DETAILED DESCRIPTION OF THE INVENTION

The features and advantages of the present invention will be more readily understood, by those of ordinary skill in the art, from reading the following detailed description. It is to be appreciated those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. Also, the disclosure of these ranges is intended as a continuous range including every value between the minimum and maximum values.

All patents, patent applications and publications referred to herein are incorporated by reference in their entirety.

A typical auto or truck body is produced from a steel sheet or a plastic or a composite substrate. For example, the fenders may be of plastic or a composite and the main portion of the body of steel. If steel is used, it is first treated with an inorganic rust-proofing compound, such as, zinc or iron phosphate and then a primer coating is applied generally by electrodeposition. Typically, these electrodeposition primers are epoxy-modified resins crosslinked with a polyisocyanate and are applied by a cathodic electrodeposition process. Optionally, a primer can be applied over the electrodeposited primer, usually by spraying, to provide better appearance of a base coating or a mono coating applied over the primer and to improve the adhesion of such coatings to the primer or both of the above. A mono coating of a pigmented coating composition then can be applied but preferably, a pigmented base coating with a clear top coating is applied to form a clear coat/color coat finish on the truck or automobile body or auto or truck part. Usually, after application, each of the coatings may be cured at ambient temperature or by baking at an elevated temperature. It is generally known that a clear top coating can be applied over the base coating and both coatings cured together-at an elevated temperature.

When refinishing automobile and truck bodies, the original OEM topcoat is usually sanded and a primer or sealer coat applied and then a mono coat or a basecoat/clear coat is applied. These coatings are usually cured at ambient temperatures or at slightly elevated temperatures, such as, 40 to 100° C.

A "clear coating composition" for automotive use is a composition that forms a transparent finish upon curing and typically has a DOI (distinctness of image) of more than 70 and a 20° gloss of more than 70. These clear coatings provide a glossy in depth appearance to the finish on the automobile or truck and therefore, are required to have good gloss and distinctness of image. Also, the clear finish also provides a protective finish that is durable and resistant to scratching, marring and chipping and also provides resistance to weathering, in particular to U.V. degradation and photo-oxidation.

A "matte clear coating composition" can also be used, for example for the interior of an automobile or truck. These matte finishes have a substantially lower gloss, for example, a 20° gloss of 20 or less and very low DOI.

Typical "primer compositions" provide adhesion to a substrate and for the novel compositions of this invention provide excellent adhesion to bare metal substrates, such as, steel and aluminum, and to treated metal substrates, such as, galvanized steel, and provide a surface to which the topcoat, such as, a pigmented mono coat or the basecoat of a base coat clear coat finish.

The term "binder" as used herein refers to the film forming constituents of the composition that include the isocyanate reactive component, i.e., having functional groups that are reactive with isocyanates and comprising active hydrogen, and optional polymeric and/or oligomeric components, polyisocyanate crosslinking agents and optional reactive diluents, such as, ketimines and aldimines and optional acrylic non-aqueous dispersions. Solvents, pigments, catalysts, rheology modifiers, antioxidants, U.V. absorbers, hindered amine light stabilizers, antioxidants, in particular disubstituted phenolic compounds, hydroperoxide decomposers, leveling agents, antifoaming agents, anti-cratering agents, adhesion promoting agents are not included in the term.

Molecular weight (both number and weight average) is determined by gel permeation chromatography utilizing a high performance liquid chromatograph supplied by Hewlett-Packard, Palo Alto, Calif. and unless otherwise stated the liquid phase used was tetrahydrofuran and the standard was polymethylmethacrylate or polystyrene.

"Tg" (glass transition temperature) is in ° C. and determined by Differential Scanning Calorimetry or calculated according to the Fox Equation.

Typically the binder of the novel composition comprises 20 to 80% by weight, based on the weight of the binder, of the isocyanate reactive component or aspartic acid derivative and 20 to 80% by weight, based on the weight of the binder, of a polyisocyanate crosslinking agent. The stochiometric ratio of isocyanate functionality to isocyanate reactive component is 0.5 to 3.0, preferably, 0.8 to 2.0 and most preferably, 1.0 to 1.5. Optionally, the binder can contain up to. 75% by weight, preferably, 5 to 60% by weight, and most preferably, 5 to 30% by weight, based on the weight of the binder, of a polymeric or oligomeric component or both wherein the component contains groups that are reactive with the polyisocyanate crosslinking agent. One preferred binder composition contains 25 to 50%, by weight of the isocyanate reactive component, 5 to 30% by weight of the polymeric or oligomeric component or both and 20 to 70% by weight of a polyisocyanate, wherein the sum of all of the components of the binder is 100%. Another preferred binder composition contains the isocyanate reactive component as the sole nucleophilic component that is reactive with the polyisocyanate.

Particular advantages of the novel coating composition of this invention is that it provides a protective clear finish that has an excellent balance between pot life and cure characteristics once applied to the object. Also, the resulting finish has good gloss and distinctness of image that provides an excellent appearance. The finish hardens in a reasonably short time after application and has excellent weatherability, in particular, resistance to U.V. degradation and photo-oxidation when properly reinforced with the appropriate additives. When the novel composition is used to refinish automobiles and trucks, it has excellent adhesion to metal substrates and cures to a tack free state in a relatively short period of time under ambient temperatures or under slightly elevated drying temperatures, for example, 40 to 100° C., that allows a coated vehicle to be moved or further processed without damage to the finish.

The novel composition of this invention can contain pigments and is useful as a pigmented mono-coat topcoat, as a pigmented base coat of a base coat/clear coat finish or as a primer or primer surfacer. Such a primer or primer surfacer cures in a relatively short period of time to allow for subsequent application of topcoats, basecoat/clear coats or monocoats. The novel composition can also be used for OEM (original equipment manufacture) of automobiles, trucks and parts thereof.

The novel composition typically is solvent based and has a solids content of film forming binder of 20 to 90% by weight, preferably, 40 to 80% by weight. It may be possible to formulate a 100% solids composition with the use of reactive diluents or when applied at high viscosities by, for example, using airless spray equipment or when used as a putty.

An aqueous liquid carrier, which typically is water but may contain other liquids, may be used in place of the solvent. Before application, a sufficient amount of liquid usually is added, for example, water or solvents, to reduce the composition to a spray viscosity. In the event the novel coating composition is an aqueous based composition, the composition typically has a pH of 6.0 to 10.0 and preferably, 7.5 to 8.5.

The present invention provides for a facile synthesis of a thermoreversible system useful as coating, where the term "thermoreversible" describes a polymeric network which upon heating breaks up which results in disintegration of the polymeric network. A typical example of such a thermoreversible coating is, for example, described in U.S. Pat. No. 5,633,389 for the formation of a hydantoin from an aspartic polyester-urea. Low molecular weight hydantoins are well known compounds and their uses as intermediates and ingredients in the chemical, pharmaceutical and consumer product industries. Certain coatings of this invention comprised of aspartic ester compounds (such as, structures II to XXVII, shown below), may undergo a thermoreversible crosslinking reaction such that the ester-backbone between urea-crosslinks is cleaved.

Surprisingly, certain aspartic compounds of this invention do not undergo a thermoreversible crosslinking reaction under conditions comparable to aspartic ester compounds. It was discovered that compounds with an amide linkage in the backbone of the molecule and hence between the urea links in the coating film, for example, compounds XXVIII–XLI of this invention after crosslinking with isocyanates, do not undergo a thermoreversible crosslinking reaction. For example, when crosslinked coating films containing aspartic ester compounds, for example, compound IX, are heated at 140° C. for 30 minutes, the films will lose a significant amount of crosslinking and become soluble in common solvents, such as, methyl ethyl ketone. The urea crosslinking, which occurs in these films under the ambient, or slightly elevated temperatures shown above, is significantly lost upon heating. Such films could be used as a temporary protection barrier, for example, for storage or transportation or other reasons not mentioned here. On the other hand, aspartic amide compounds (for example, XXVIII–XLI) crosslinked with isocyanates do not lose the urea crosslinking under the same conditions. This makes it possible to engineer novel coating compositions with varying degrees of thermoreversibility by using, for example, mixtures of aspartic amides and aspartic esters.

The isocyanate reactive component of the novel composition is an amine derivative and has the formula (I)

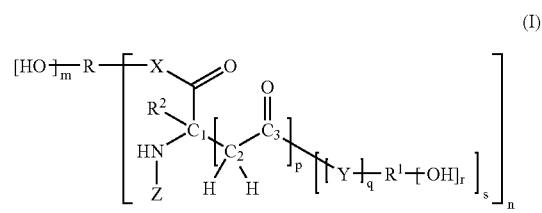

wherein

R is a hydrocarbon radical obtained by removing (m+n) hydrogen atoms from a $C_1$ to $C_{20}$ linear or branched alkyl group, or a $C_5$ to $C_{16}$ cycloaliphatic group; alternatively, R is a residue obtained by removing n amino groups from a polyether polyamine with m equal to 0 having a functionality of n and a number average molecular weight of less than 600, wherein the amino groups are attached to primary carbon atoms and the ether groups are separated by at least two carbon atoms;

m equals 0 to 4, and m preferably equals 0, 1 or 2, and n, on average, equals 1 to 4, and preferably, n, on average, equals 1 and 2, with the proviso that m cannot be 0 unless n equals at least 2 if r equals 0 and Z does not contain an OH-group, n equals 1 and r equals 1 and Z does or does not contain an OH-group, or n equals 1, r equals 0 and Z contains at least one OH-group;

X and Y each can be independently O or $NR^3$;

$R^3$ is equal to H, or $C_1$ to $C_{20}$ linear or branched alkyl group, a $C_5$ to $C_{16}$ cycloaliphatic group, or $R^3$ is equal to $C_3$=O if s=0, i.e., the compound is a cyclic imide;

Z is selected from a $C_1$ to $C_{20}$ linear or branched alkyl group, a $C_5$ to $C_{16}$ cycloaliphatic group, or an OH-group containing linear, branched or cycloaliphatic alkyl group, preferred groups for Z are methyl, propyl, n-butyl, iso-butyl, sec-butyl, tert-butyl, or cyclohexyl; or Z comprises a fragment of the structure —$CH_2$—$CHR^4$—$R^5$, with $R^4$ equal to H, or $C_1$ to $C_{20}$ linear or branched alkyl group, or a $C_5$ to $C_{16}$ cycloaliphatic group and $R^5$ equal to —CN or —C(=O)$OR^6$, with $R^6$ equal to H, or $C_1$ to $C_{20}$ linear or branched alkyl group, or a $C_5$ to $C_{16}$ cycloaliphatic group;

p and q are equal to 0 or 1, if p and q equal to 1, the —NH-Z fragment can be bound to either $C_1$ or $C_2$, and mixtures of compounds and isomers are commonly utilized by this invention;

s is equal to 0 or 1, with the proviso that s can only be 0 if p equals 1 and $X=NR^3$ wherein $R^3$ equals $C_3=O$ (cyclic imide);

$R^2$ is H or independently selected from a $C_1$ to $C_{20}$ linear or branched alkyl group, or a $C_5$ to $C_{16}$ cycloaliphatic group;

$R^1$ is a hydrocarbon radical obtained by removing (q+r) hydrogen atoms from a $C_1$ to $C_{20}$ linear or branched alkyl group, or a $C_5$ to $C_{16}$ cycloaliphatic group; and r is equal to 0 to 4, and r preferably, equal to 0 or 1.

The following formulas illustrate particularly useful isocyanate reactive components which are amine compounds that are useful in the novel coating composition of this invention which provide finishes, in particular, protective clear finishes that have an excellent balance between pot life and cure characteristics on application.

Preferred amine compounds used in the novel coating composition of this invention are for example the following structures (II) to (XXVII). These structures are defined by formula (I) wherein m=0, X=O, Y=O, $R^2$=H, n=2, p=1, q=1, r=0, s=1, wherein R, $R^1$ are as defined above, and Z is selected from a $C_1$ to $C_{20}$ linear or branched alkyl group, or a $C_5$ to $C_{16}$ cycloaliphatic group, preferred groups for Z are methyl, propyl, n-butyl, iso-butyl, sec-butyl, tert-butyl, or cyclohexyl.

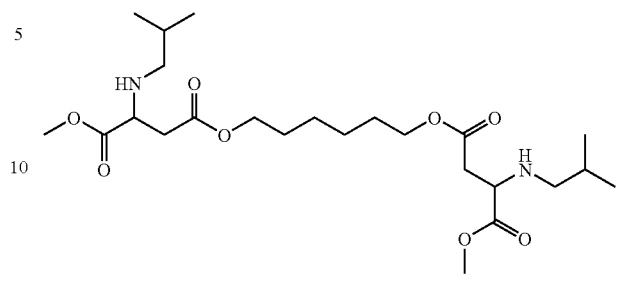
(V)

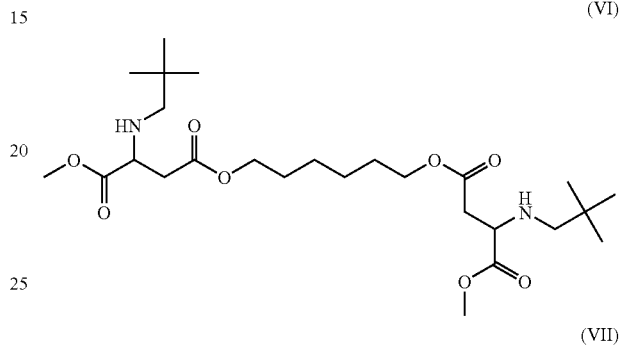
(VI)

(VII)

(VIII)

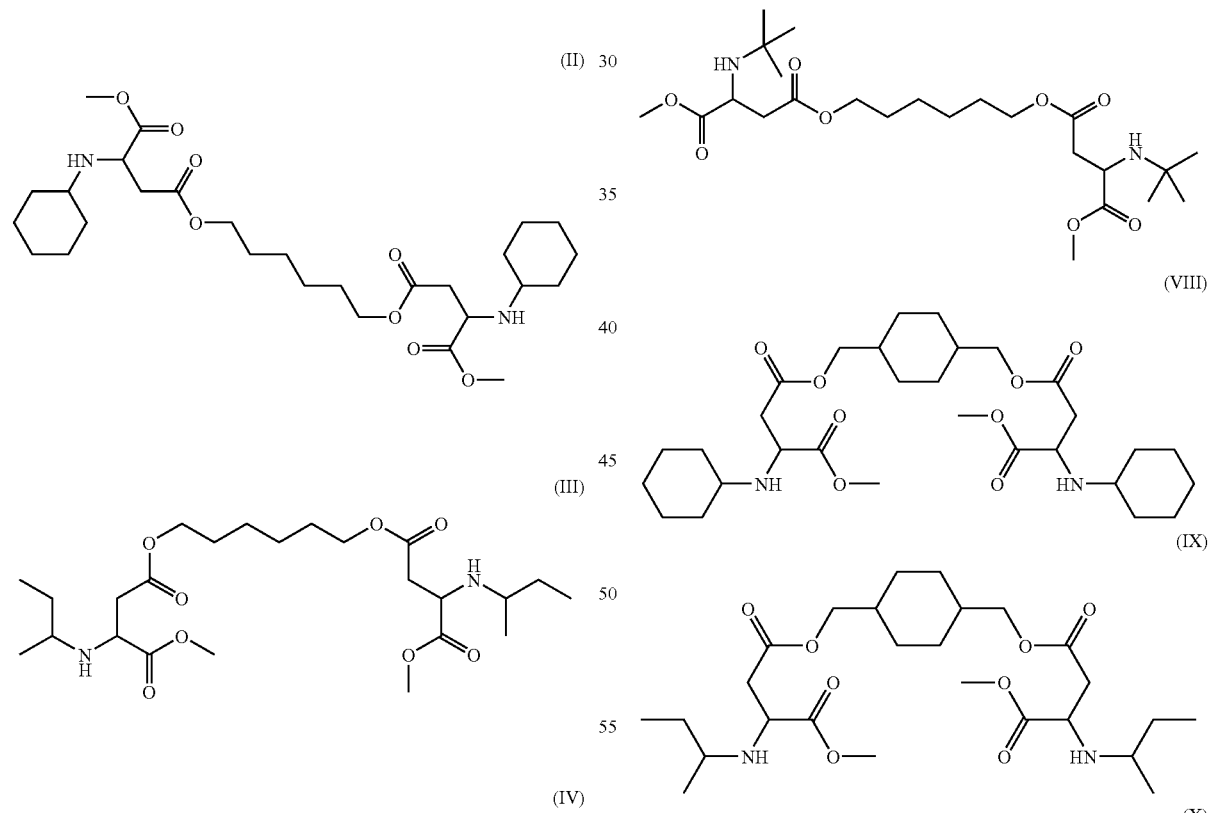
(II)

(III)

(IV)

(IX)

(X)

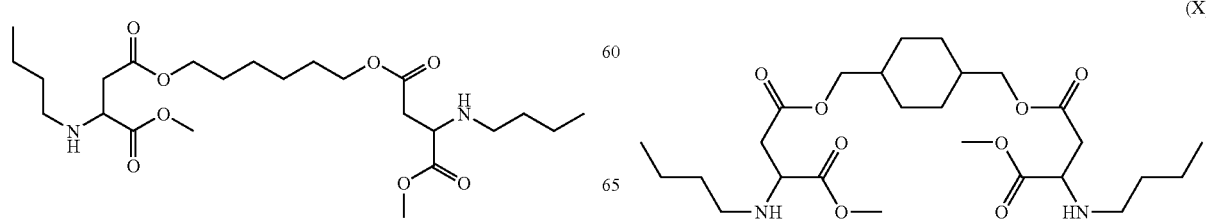

-continued
(XI)
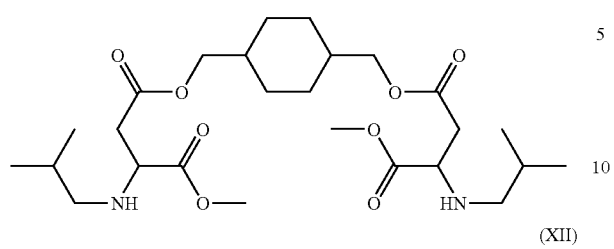
(XII)
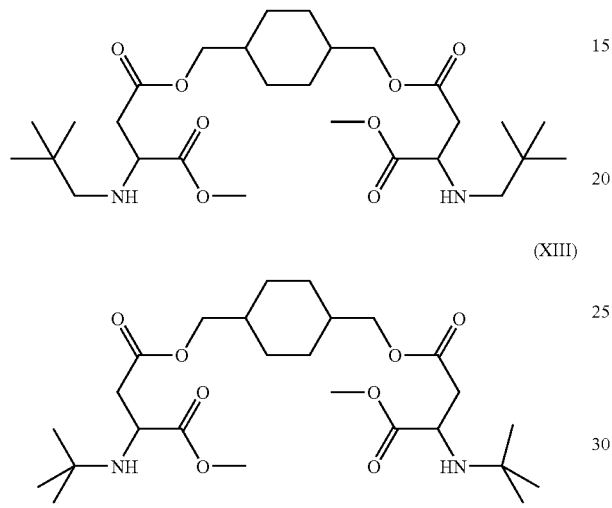
(XIII)
(XIV)
(XV)
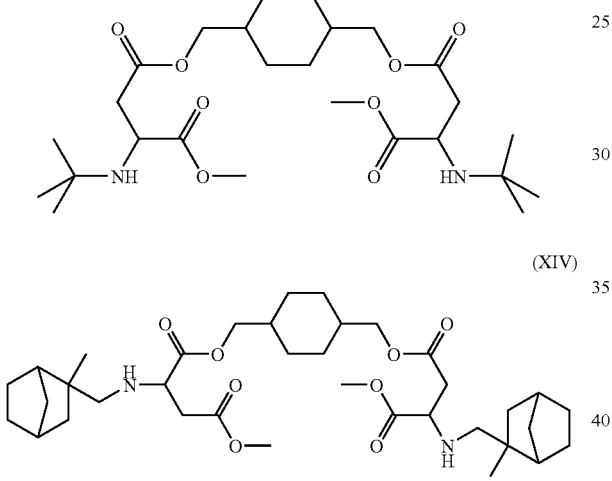
(XVI)
-continued
(XVII)
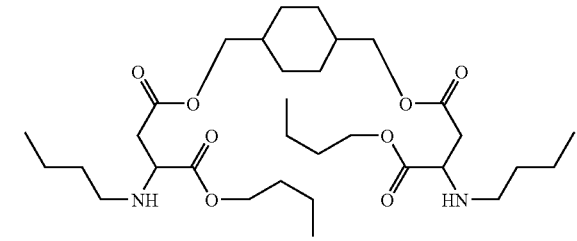
(XVIII)
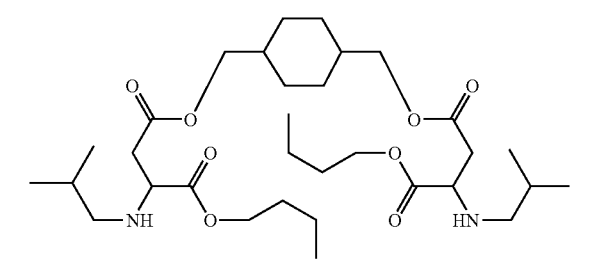
(XIX)
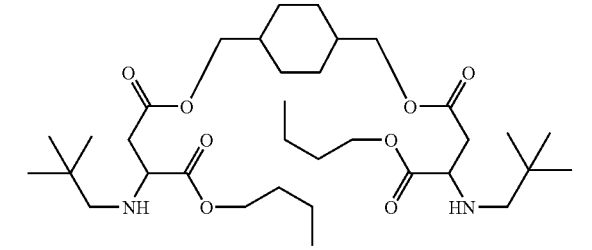
(XX)
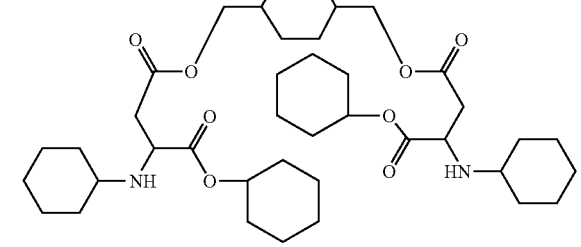
(XXI)
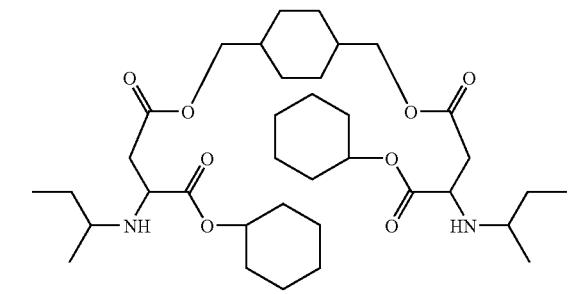

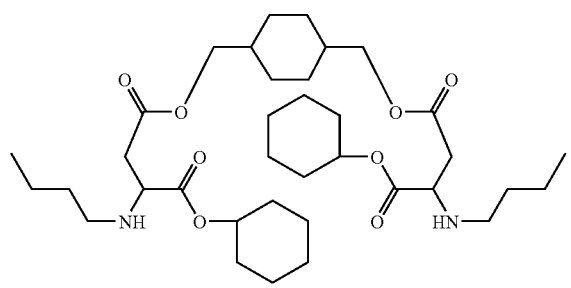
(XXII)

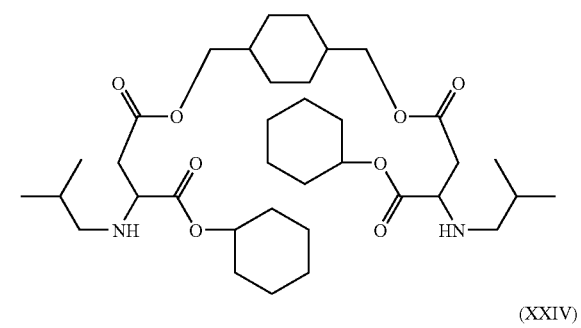
(XXIII)

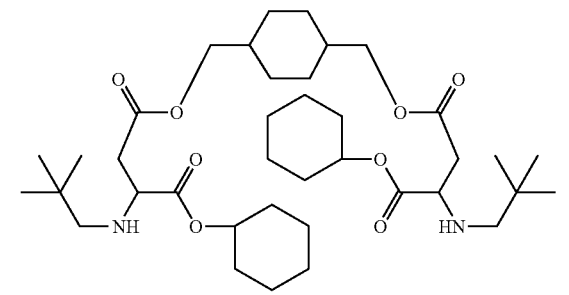
(XXIV)

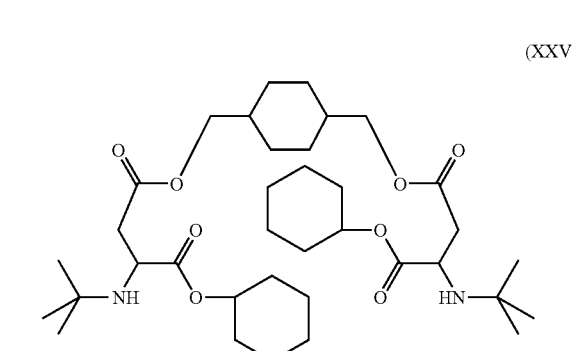
(XXV)

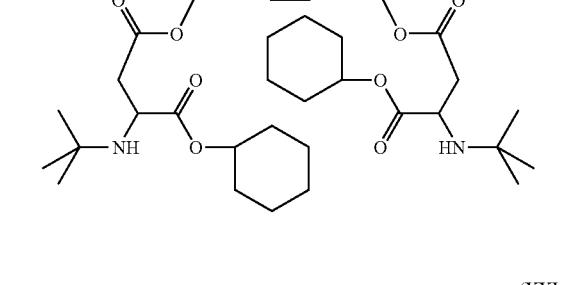
(XXVI)

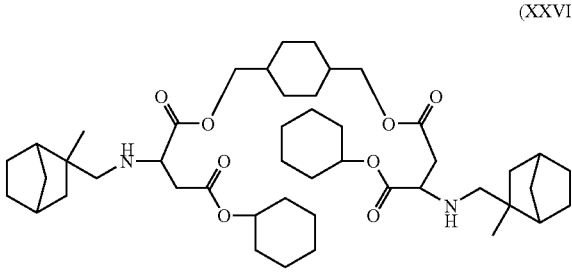

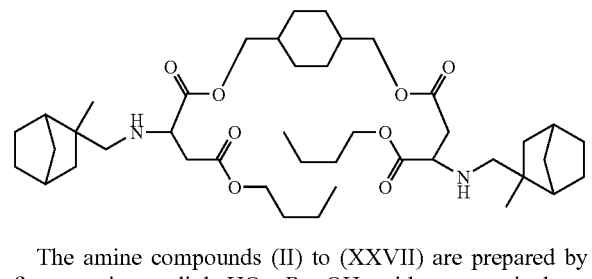
(XXVII)

The amine compounds (II) to (XXVII) are prepared by first reacting a diol, HO—R—OH, with two equivalents maleic anhydride, followed by esterification to form the bis-maleate. Further reaction with a primary amine component yields the secondary amine compound of this invention. The reaction temperature, conditions and reactant concentration is selected to favor the formation of the double addition product. However, small amounts of half reacted bis-maleate, i.e., an amine-maleate intermediate, may be present in the final product.

In another preferred embodiment, this invention relates to compounds with, for example, structures (XXVIII) to (XLIII). These structures are defined by formula (I) with $m=0$, $n=2$, $X=NH$, $Y=O$, $R^2=H$, $p=1$, $q=1$, $r=0$, $s=1$, wherein R, $R^1$ are as defined above, and Z is selected from a $C_1$ to $C_{20}$ linear or branched alkyl group, or a $C_5$ to $C_{16}$ cycloaliphatic group, preferred groups for Z are methyl, propyl, n-butyl, iso-butyl, sec-butyl, tert-butyl, or cyclohexyl, preferred groups for $R^1$ are methyl, ethyl, propyl, n-butyl, iso-butyl, or cyclohexyl.

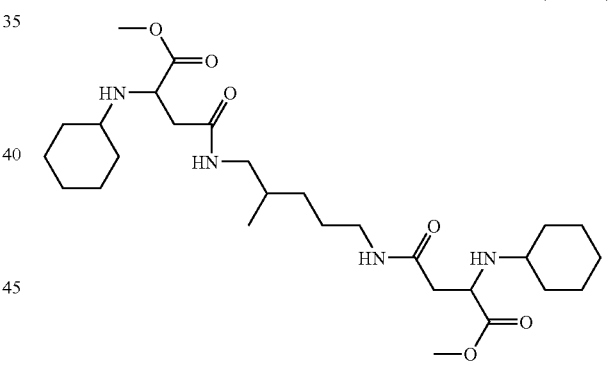
(XXVIII)

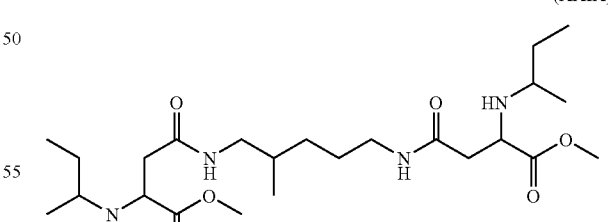
(XXIX)

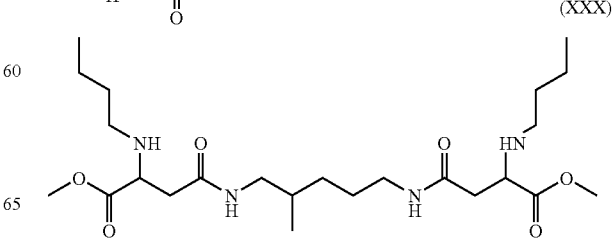
(XXX)

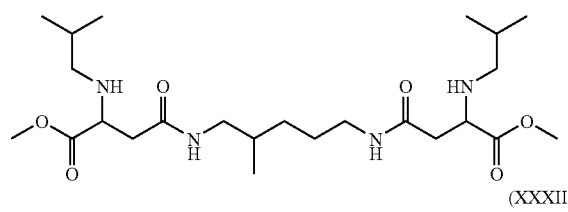
(XXXI)

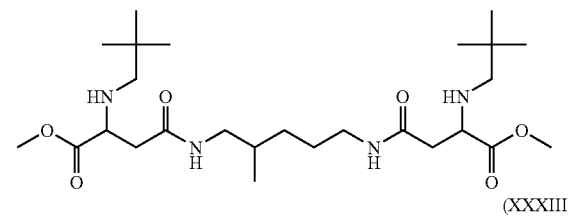
(XXXII)

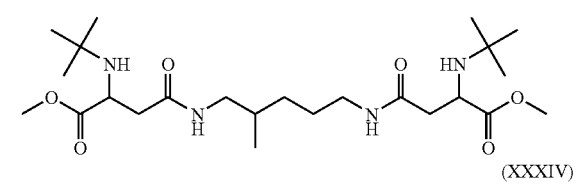
(XXXIII)

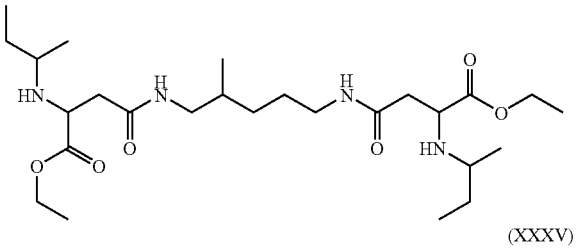
(XXXIV)

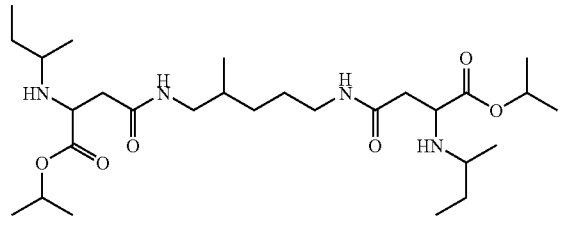
(XXXV)

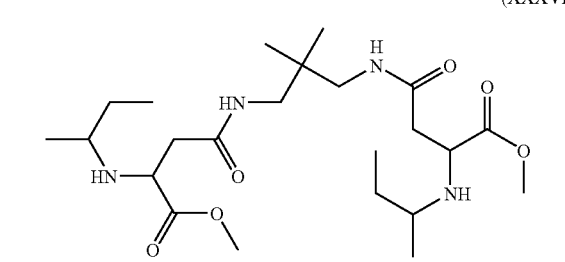
(XXXVI)

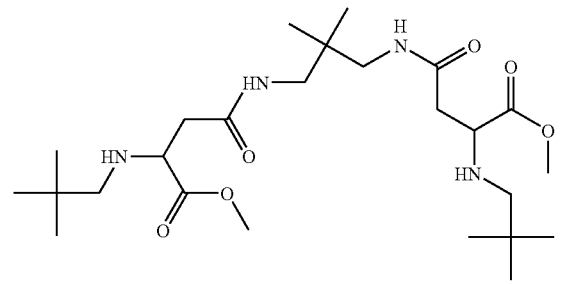

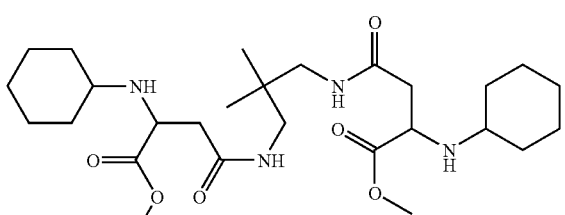
(XXXVIII)

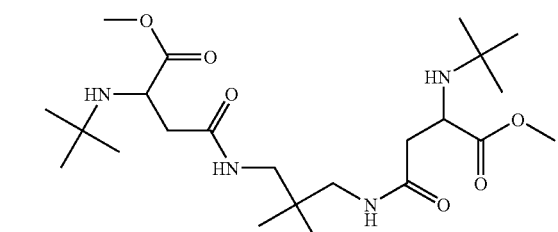
(XXXIX)

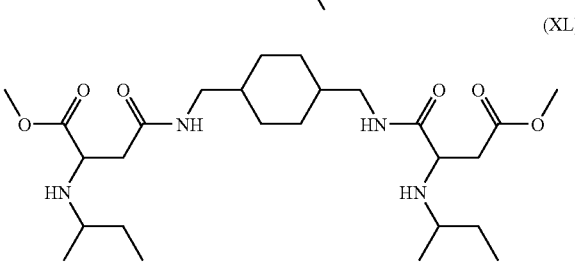
(XL)

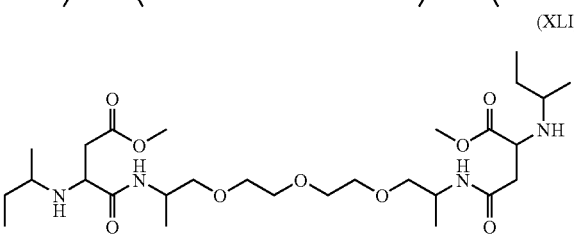
(XLI)

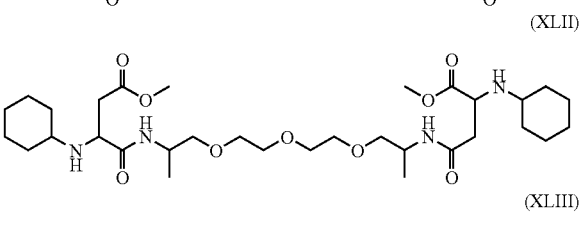
(XLII)

(XLIII)

The amine compounds (XXVIII) to (XLIII) are prepared by first reacting a diamine, $H_2N—R—NH_2$, with two equivalents maleic anhydride to form the bis-maleamic acid, followed by esterification of the carboxylic acid groups. Further reaction with a primary amine component yields the secondary amine compound of this invention. The reaction temperature, conditions and reactant concentration is selected to favor the formation of the double addition product. However, small amounts of half reacted bis-maleate, i.e. an amine-maleate intermediate, may be present in the final product. Compounds (XLI) and (XLIII) are typically formed using a commercial product, Jeffamine®-HK511, which is a mixture of difunctional primary amines having an average molecular weight of approximately 220 and containing both oxyethylene and oxypropylene groups. The resulting compounds (XLI) and (XLII) will each be a mixture of compounds having these groups.

Another preferred embodiment of the present invention relates to compounds with for example structure (XLIV). This structure is defined by formula (I) with m=0, n=2, X=NR$^3$, R$^2$=H, p=1, s=0, wherein R is defined above, R$^3$ equals C$_3$=O, and Z is selected from a C$_1$ to C$_{20}$ linear or branched alkyl group, or a C$_5$ to C$_{16}$ cycloaliphatic group, preferred groups for Z are methyl, propyl, n-butyl, iso-butyl, sec-butyl, tert-butyl, or cyclohexyl.

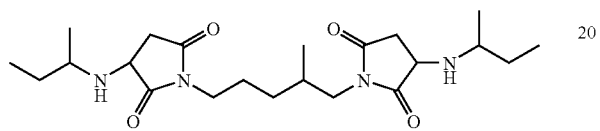

(XLIV)

Amine compounds similar to (XLIV) are prepared by first reacting a diamine, H$_2$N—R—NH$_2$, with two equivalents maleic anhydride to form the bis-maleamic acid, followed by cyclization to the bis-maleimide. Further reaction with a primary amine component yields the secondary amine compound of this invention. The reaction temperature, conditions and reactant concentration is selected to favor the formation of the double addition product.

Another preferred embodiment of this invention relates to compounds with structure (XLV), having one maleamic ester unit (analogous to XXIX) and one maleimide unit (analogous to (XLIV) within the same molecule, isomers thereof, as well as mixtures of these compounds with either of the aforementioned bis-maleamic ester or bis-maleimide compounds.

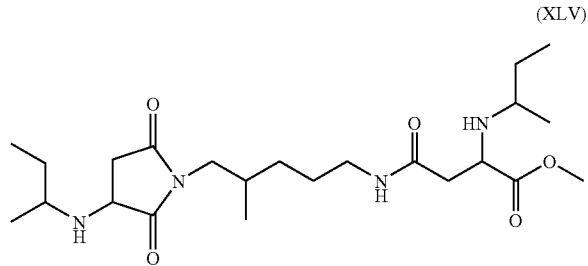

(XLV)

Compounds, such as, (XLV) are often formed as side-products in the synthesis of bis-maleate-based compounds (XXVIII–XLIII).

Another preferred embodiment of this invention relates to compounds with, for example, structures (XLVI) and (XLVII). These structures are defined by formula (I) with m=0, n=2, X=NR$^3$, Y=O, p=1, q=0, r=0, s=1, wherein R, R$^1$ and R$^2$ are as defined above, R$^3$ equals Me or another alkyl group, and Z is selected from a C$_1$ to C$_{20}$ linear or branched alkyl group, or a C$_5$ to C$_{16}$ cycloaliphatic group. Since the amide-N is methylated in compounds XLIV and XLV, these compounds will not undergo imide formation such as the aforementioned aspartic amides.

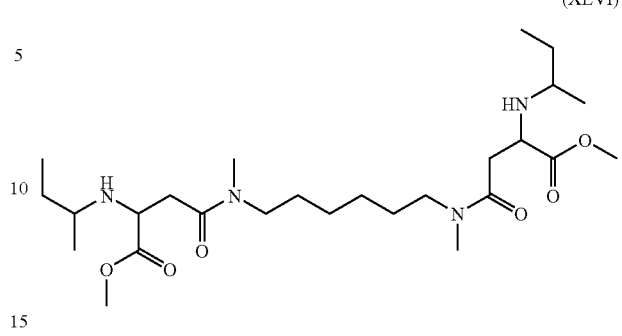

(XLVI)

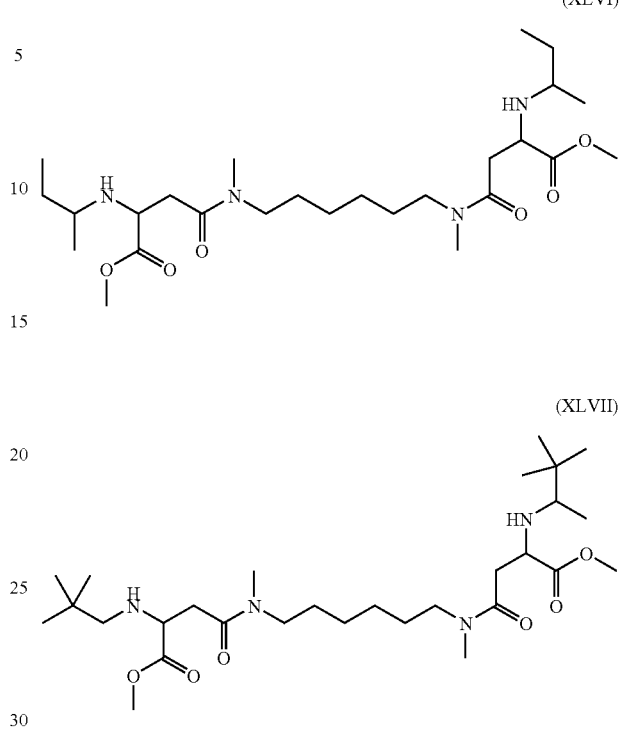

(XLVII)

The amine compounds (XLVI) and (XLVII) are prepared by first reacting a diamine, HN(Me)—R—N(Me)H, with two equivalents maleic anhydride to form the bis-maleamic acid, followed by esterification of the carboxylic acid groups. Further reaction with a primary amine component yields the secondary amine compound of this invention. The reaction temperature, conditions and reactant concentration is selected to favor the formation of the double addition product. However, small amounts of half reacted bis-maleate, i.e., an amine-maleate intermediate, may be present in the final product.

Another preferred embodiment of this invention relates to compounds with, for example, structures (XLVIII) to (LI). These structures are defined by formula (I) with m=0, n=2, X=O, p=0, q=0, r=0, s=1, wherein R, R$^1$ and R$^2$ are as defined above, and Z is selected from a C$_1$ to C$_{20}$ linear or branched alkyl group, or a C$_5$ to C$_{16}$ cycloaliphatic group, or Z comprises a fragment of the structure —CH$_2$—CHR$^4$—R$^5$, with R$^4$ equal to H, or C$_1$ to C$_{20}$ linear or branched alkyl group, or a C$_5$ to C$_{16}$ cycloaliphatic group and R$^5$ equal to —CN or —C(=O)OR$^6$, with R$^6$ equal to H, or C$_1$ to C$_{20}$ linear or branched alkyl group, or a C$_5$ to C$_{16}$ cycloaliphatic group.

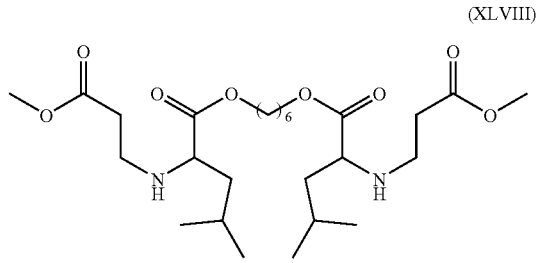

(XLVIII)

(XLIX)
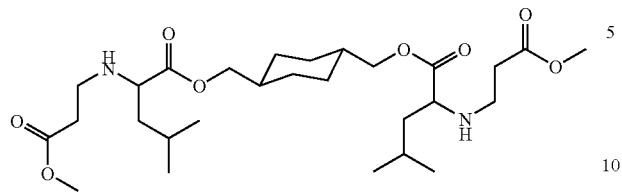

(L)
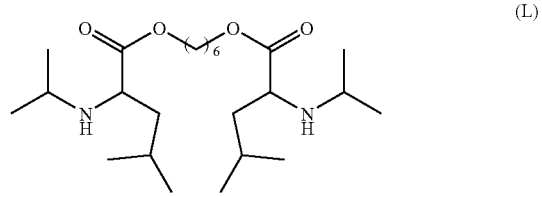

(LI)
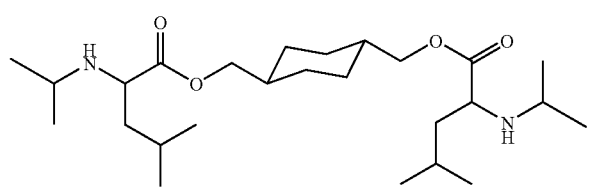

The amine compounds (XLVIII) to (LI) are prepared as isomeric mixtures by first reacting a diol, HO—R—OH, with two equivalents of an amino acid, followed by functionalization of the amino group via either Michael addition to a Michael acceptor (see XLVIII or XLIX), or via reductive amination (see L or LI). The reaction temperature, conditions and reactant concentration is selected to favor the formation of the double addition product, however small amounts of half-reacted intermediate, comprising both functionalized secondary amine and unreacted primary amine groups, may be present.

Another preferred embodiment of this invention relates to compounds with for example structures (LII) and (LIII). These structures are defined by formula (I) with m=1, n=1, X=O, p=0, q=0, r=0, s=1, wherein R, $R^1$ and $R^2$ are as defined above, and Z is selected from a $C_1$ to $C_{20}$ linear or branched alkyl group, or a $C_5$ to $C_{16}$ cycloaliphatic group, or Z comprises a fragment of the structure —$CH_2$—$CHR^4$— $R^5$, with $R^4$ equal to H, or $C_1$ to $C_{20}$ linear or branched alkyl group, or a $C_5$ to $C_{16}$ cycloaliphatic group and $R^5$ equal to —CN or —C(=O)$OR^6$, with $R^6$ equal to H, or $C_1$ to $C_{20}$ linear or branched alkyl group, or a $C_5$ to $C_{16}$ cycloaliphatic group.

(LII)
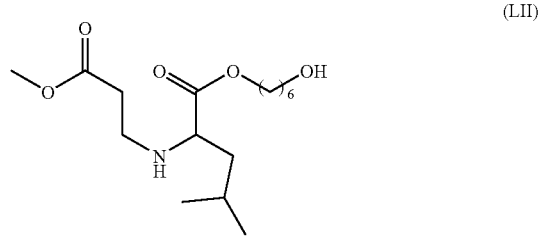

(LIII)
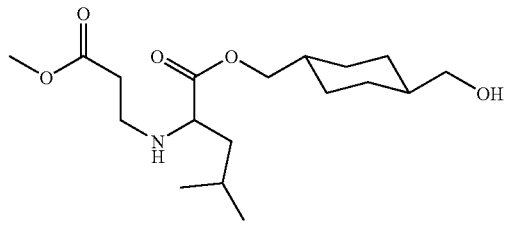

The amine compounds (LII) and (LIII) are prepared as isomeric mixtures by first reacting a diol, HO—R—OH, with one equivalent of an amino acid, followed by functionalization of the amino group via either Michael addition to a Michael acceptor (see LII), or via reductive amination (see LIII).

Another preferred embodiment of this invention relates to compounds with for example structure (LIV). These structures are defined by formula (I) with m=1, n=1, X=O, Y=O, p=1, q=1, r=0, s=1, wherein R, $R^1$ and $R^2$ are as defined above, and Z is selected from a $C_1$ to $C_{20}$ linear or branched alkyl group, or a $C_5$ to $C_{16}$ cycloaliphatic group.

(LIV)
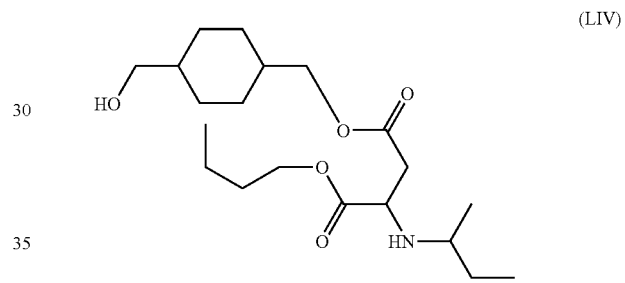

The amine compounds (LIV) are prepared as isomeric mixtures by reacting a diol, HO—R—OH, with one equivalent of maleic anhydride, followed by esterification of the carboxylic acid group and Michael addition of a primary amine to the double bond.

Yet another preferred embodiment of this invention relates to aminoalcohol compounds with for example structures (LV–LXV). These structures are defined by formula (I) with m=0, n=1, X=O, Y=$NR^3$, p=1, q=1, r=0, s=1, wherein R, $R^1$ and $R^2$ are as defined above, $R^2$ can equal $R^3$, and Z is an OH-group containing linear, branched or cycloaliphatic alkyl group.

(LV)
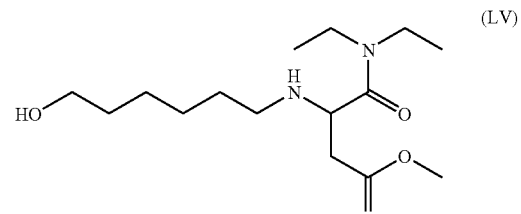

(LVI)
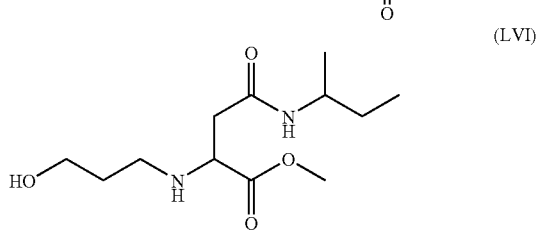

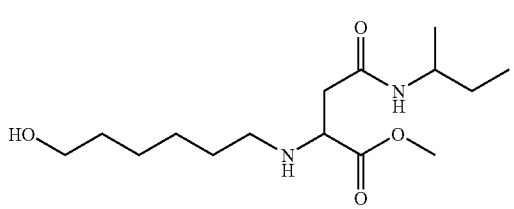
(LVII)

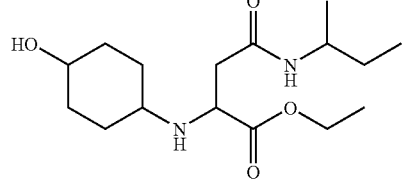
(LXIV)

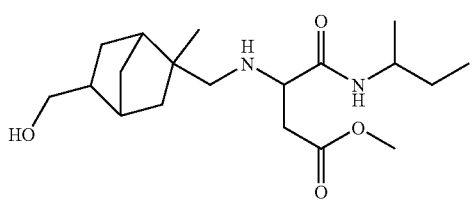
(LVIII)

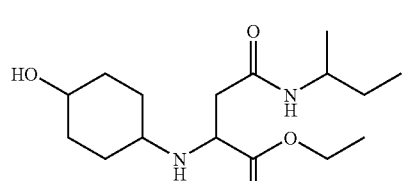
(LXV)

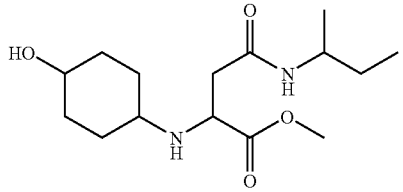
(LIX)

Aminoalcohol compounds such as (LV–LXV) are prepared by first reacting a primary amine with one equivalent of maleic anhydride, followed by esterification of the carboxylic acid group to yield unsaturated amide-ester. Michael addition of an amino-alcohol to the double bond yields the final product as isomeric mixture.

Another preferred embodiment of this invention relates to compounds with for example structures (LXVI). These structures are defined by formula (I) with m=1, n=1, X=O, Y=O, p=1, q=1, r=1, s=1, wherein R, R¹ and R²are as defined above and R preferably equals R¹, and Z is selected from a $C_1$ to $C_{20}$ linear or branched alkyl group, or a $C_5$ to $C_{16}$ cycloaliphatic group.

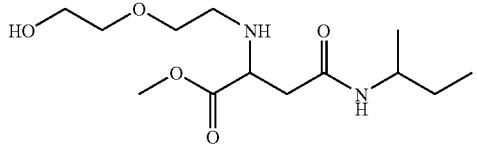
(LX)

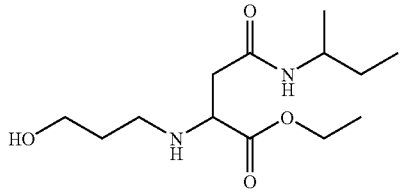
(LXI)

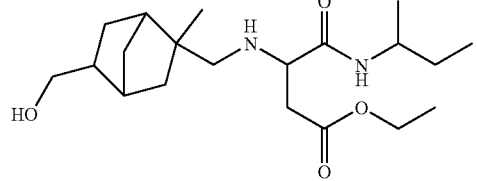
(LXVI)

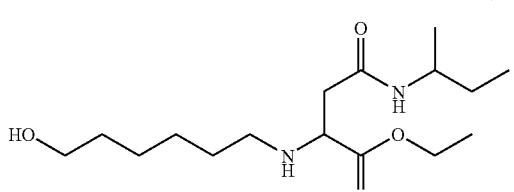
(LXII)

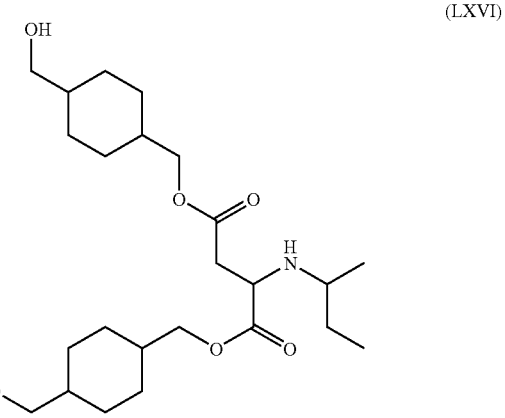

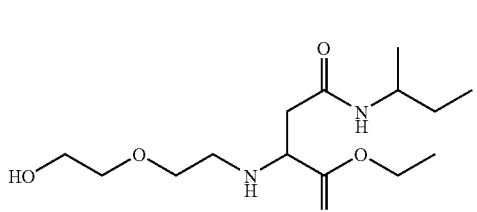
(LXIII)

Amine-diols analogous to compound (LXVI) can be prepared by reacting two equivalents of a diol, HO—R—OH, with one equivalent of maleic acid under acid catalysis, followed addition of a primary amine to the maleate double bond.

The novel coating composition can contain optional polymeric components. These components have groups that are reactive with isocyanate and can be used in an amount of up to 75% by weight, preferably, 1 to 60% by weight, based on the weight of the binder. One preferred polymeric component is an acrylic polymer. Typically useful acrylic polymers have a number average molecular weight of about 5,000 to 50,000, a Tg of 10 to 80° C. and contain moieties, such as acetoacetate, aldimine, ketimine, mercaptan, hydroxyl, carboxyl, glycidyl and amino groups. Typically useful acrylic polymers are those known in the art and are polymers of two or more of the following: linear alkyl (meth)acrylates having 1 to 12 carbon atoms in the alkyl group, cyclic or branched alkyl (meth)acrylates having 3 to 12 carbon atoms in the alkyl group including isobornyl (meth)acrylate, hydroxy alkyl (meth)acrylates having 1 to 4 carbon atoms in the alkyl group, glycidyl (meth)acrylate, hydroxy amino alkyl (meth) acrylates having 1 to 4 carbon atoms in the alkyl group, and can contain styrene, alpha methyl styrene, vinyl toluene, (meth)acrylonitrile (meth)acryl amides, (meth)acrylic acid, (meaning both acrylic acid and methacrylic acid) trimethoxysilylpropyl (meth)acrylate and the like.

Preferred are hydroxy functional acrylic polymers having a hydroxy equivalent weight of 300 to 1300 and are polymers of hydroxy alkyl (meth)acrylates and one or more of the aforementioned monomers. One preferred hydroxy containing acrylic polymer contains 35 to 50% by weight styrene, 15 to 25% by weight ethylhexyl methacrylate and 15 to 20% by weight isobornyl methacrylate and 20 to 30% by weight hydroxyethyl methacrylate. A particularly preferred acrylic polymer contains 37% styrene, 20% by weight 2-ethylhexyl methacrylate and 17.5% by weight of isobornyl methacrylate and 25.5% by weight hydroxyethyl methacrylate.

Acrylic oligomers having a number average molecular weight of 300 to 3,000 of the aforementioned monomeric components also can be used as the optional polymeric component. By using monomers and reactants well known to those skilled in the art, these oligomers can have the one or more of the following groups that are reactive with isocyanate: hydroxyl, carboxyl, glycidyl, amine, aldimine, phosphoric acid and ketimine. Typically useful acrylic oligomers are disclosed in FA 1048 Ser. No. 10/617,585 filed Jul. 11, 2003, Publication No. U.S. 2004-001009, published on Jan. 15, 2004, which is hereby incorporated by reference.

Polyesters can also be used as the optional polymeric component, such as, hydroxyl or carboxyl terminated or hydroxyl or carboxyl containing polyesters. The following are typically useful polyesters or ester oligomers: polyesters or oligomers of caprolactone diol and cyclohexane dimethylol, polyesters or oligomers of tris-hydroxy ethylisocyanurate and caprolactone, polyesters or oligomers of trimethylol propane, phthalic acid or anhydride and ethylene oxide, polyesters or oligomers of pentaerythritol, hexahydrophthalic anhydride and ethylene oxide, polyesters or oligomers of pentaerythritol, hexahydrophthalic anhydride and butylene oxide, such as those shown in U.S. Pat. No. 6,221,494 B1 which is hereby incorporated by reference.

The aforementioned polyesters and oligomers can be reacted with an organic isocyanate to form urethane polymers and oligomers that can be used as the optional polymeric component in the novel composition.

One useful urethane oligomer that can used in the novel composition is formed by reacting an aliphatic polyisocyanate with an aliphatic or cycloaliphatic monohydric alcohol and subsequently reacting the resulting composition with a hydroxy functional aliphatic carboxylic acid until all of the isocyanate groups have been reacted. One useful polyurethane oligomer comprises the reaction product of the isocyanurate of hexane diisocyanate, cyclohexanol and dimethylol propionic acid. A water dispersible oligomer can be formed using conventional techniques know to those skilled in the art.

Optionally, an oligomeric component having a number average molecular weight of 300 to 3,000 having reactive groups that crosslink with an isocyanate, where the reactive groups are hydroxyl, carboxyl, glycidyl, amine, aldimines, phosphoric acid, ketimine and any mixtures thereof can be added to the novel composition.

Typically useful organic polyisocyanates crosslinking agents that can be used in the novel composition of this invention include aliphatic polyisocyanates, cycloaliphatic polyisocyanates and isocyanate adducts.

Examples of suitable aliphatic and cycloaliphatic polyisocyanates that can be used include the following: 4,4'dicyclohexyl methane diisocyanate, ("$H_{12}$MDI"), trans-cyclohexane-1,4-diisocyanate, 1,6-hexamethylene diisocyanate ("HDI"), isophorone diisocyanate,("IPDI"), other aliphatic or cycloaliphatic di-, tri- or tetra-isocyanates, such as, 1,2-propylene diisocyanate, tetramethylene diisocyanate, 2,3-butylene diisocyanate, octamethylene diisocyanate, 2,2,4-trimethyl hexamethylene diisocyanate, dodecamethylene diisocyanate, omega-dipropyl ether diisocyanate, 1,3-cyclopentane diisocyanate, 1,2 cyclohexane diisocyanate, 1,4 cyclohexane diisocyanate, 4-methyl-1,3-diisocyanatocyclohexane, dicyclohexylmethane-4,4'-diisocyanate, 3,3'-dimethyl-dicyclohexylmethane 4,4'-diisocyanate, polyisocyanates having isocyanurate structural units, such as, the isocyanurate of hexamethylene diisocyanate and the isocyanurate of isophorone diisocyanate, the adduct of 2 molecules of a diisocyanate, such as, hexamethylene diisocyanate, uretidiones of hexamethylene diisocyanate, uretidiones of isophorone diisocyanate and a diol, such as, ethylene glycol, the adduct of 3 molecules of hexamethylene diisocyanate and 1 molecule of water, allophanates, trimers and biurets of hexamethylene diisocyanate, allophanates, trimers and biurets of isophorone diisocyanate and the isocyanurate of hexane diisocyanate.

Tri-functional isocyanates also can be used, such as, Desmodur® N 3300, trimer of hexamethylene diisocyanate, Desmodur® 3400, trimer of isophorone diisocyanate, Desmodur® 4470 trimer of isophorone diisocyanate, these trimers are sold by Bayer Corporation. A trimer of hexamethylene diisocyanate sold as Tolonate® HDT from Rhodia Corporation is also suitable.

An isocyanate functional adduct can be used, such as, an adduct of an aliphatic polyisocyanate and a polyol. Also, any of the aforementioned polyisocyanates can be used with a polyol to form an adduct. Polyols, such as, trimethylol alkanes, particularly, trimethylol propane or ethane can be used to form an adduct.

The novel composition can contain 1 to 30% by weight, based on the weight of the binder of acrylic NAD (non-aqueous dispersed) resins. These NAD resins typically are high molecular weight resins having a crosslinked acrylic core with a Tg between 20 to 100° C. and attached to the core are low Tg stabilizer segments. A description of such NADs is found in Antonelli et al. U.S. Pat. No. 4,591,533 and in Barsotti et al. U.S. Pat. No. 5,763,528 which patents are hereby incorporated by reference.

Optionally, a catalyst is used in the novel composition to reduce curing time and temperature and allow curing of the coating at ambient temperatures. Useful catalysts include alkyl carboxylic acids having 1 to 12 carbon atoms in the alkyl group, such as, acetic acid, formic acid, glycolic acid; aromatic acids, such as, benzoic acid; salicylic acid; and oligomers having pendant acid groups.

The coating composition optionally includes a catalytic amount of a catalyst for modifying the curing process. Generally, in the range of about 0.001 percent to about 5 percent, preferably in the range of from 0.005 percent to 2 percent, more preferably in the range of from 0.01 percent to 1 percent of the catalyst is utilized, all in weight percent based on the total weight of crosslinkable and crosslinking component solids. A wide variety of catalysts can be used, such as, tin compounds, including dibutyl tin dilaurate and dibutyl tin diacetate. These catalysts can be used alone or in conjunction with the carboxylic acids described above, such as, acetic acid. One of the commercially available catalysts, sold under the trademark, Fastcat® 4202 dibutyl tin dilaurate by Elf-Atochem North America, Inc. Philadelphia, Pa., is particularly suitable.

If used as a clear coat or mono-coat, the novel composition optionally contains about 0.1 to 5% by weight, based on the weight of the binder, of ultraviolet light absorbers. Typically useful ultraviolet light absorbers include hydroxyphenyl benzotriazols, such as, 2-(2-hydroxy-5-methylphenyl)-2H-benzotriazole, 2-(2-hydroxy-3,5-di-tert.amyl-phenyl)-2H-benzotriazole, 2[2-hydroxy-3,5-di(1,1-dimethylbenzyl)phenyl]-2H-benzotriazole, reaction product of 2-(2-hydroxy-3-tert.butyl-5-methyl propionate)-2H-benzotriazole and polyethylene ether glycol having a weight average molecular weight of 300, 2-(2-hydroxy-3-tert.butyl-5-iso-octyl propionate)-2H-benzotriazole; hydroxyphenyl s-triazines, such as, 2-[4((2,-hydroxy-3-dodecyloxy/tridecyloxypropyl)-oxy)-2-hydroxyphenyl]-4,6-bis(2,4-dimethylphenyl)-1,3,5-triazine, 2-[4(2-hydroxy-3-(2-ethylhexyl)-oxy)-2-hydroxyphenyl]4,6-bis(2,4-dimethylphenyl)1,3,5-triazine, 2-(4-octyloxy-2-hydroxyphenyl)-4,6-bis(2,4-dimethylphenyl)-1,3,5-triazine; hydroxybenzophenone U.V. absorbers, such as, 2,4-dihydroxybenzophenone, 2-hydroxy-4-octyloxybenzophenone, and 2-hydroxy-4-dodecyloxybenzophenone.

If used as a clear coat or mono-coat, the novel composition optionally contains about 0.1 to 5% by weight, based on the weight of the binder, of a di-substituted phenol antioxidant or a hydroperoxide decomposer. Typically useful antioxidants include tetrakis[methylene(3,5-di-tert-butylhydroxy hydrocinnamate)]methane, octadecyl 3,5-di-tert-butyl-4-hydroxyhydrocinnamate, tris(2,4-di-tert-butylphenyl) phosphite, 1,3,5-tris(3,5-di-tert-butyl-4-hydroxybenzyl)-1,3,5-triazine-2,4,6(1H,3H,5H)-trione and benzenepropanoic acid, 3,5-bis(1,1-dimethyl-ethyl)-4-hydroxy-C7–C9 branched alkyl esters. Typically useful hydroperoxide decomposers include Sanko® HCA (9,10-dihydro-9-oxa-10-phosphenanthrene-10-oxide), triphenyl phosphate and other organo-phosphorous compounds, such as, Irgafos® TNPP from Ciba Specialty Chemicals, Irgafos® 168, from Ciba Specialty Chemicals, Ultranox® 626 from GE Specialty Chemicals, Mark PEP-6 from Asahi Denka, Mark HP-10 from Asahi Denka, Irgafos® P-EPQ from Ciba Specialty Chemicals, Ethanox 398 from Albemarle, Weston 618 from GE Specialty Chemicals, Irgafos® 12 from Ciba Specialty Chemicals, Irgafos® 38 from Ciba Specialty Chemicals, Ultranox® 641 from GE Specialty Chemicals and Doverphos® S-9228 from Dover Chemicals.

If used as a clear coat or mono-coat, the novel composition optionally contains about 0.1–5% by weight, based on the weight of the binder, of hindered amine light stabilizers. Typically useful hindered amine light stabilizers include N-(1,2,2,6,6-pentamethyl-4-piperidinyl)-2-dodecyl succinimide, N(1 acetyl-2,2,6,6-tetramethyl-4-piperidinyl)-2-dodecyl succinimide, N-(2hydroxyethyl)-2,6,6,6-tetramethylpiperidine-4-ol-succinic acid copolymer, 1,3,5 triazine-2,4,6-triamine, N,N'''-[1,2-ethanediybis[[[4,6-bis[butyl(1,2,2,6,6-pentamethyl-4-piperidinyl)amino]-1,3,5-triazine-2-yl]imino]-3,1-propanediyl]]bis[N,N'''-dibutyl-N',N'''-bis(1,2,2,6,6-pentamethyl4-piperidinyl)], poly-[[6-[1,1,3,3-tetramethylbutyl)-amino]-1,3,5-trianzine-2,4-diyl][2,2,6,6-tetramethylpiperidinyl)-imino]-1,6-hexane-diyl[(2,2,6,6-tetramethyl-4-piperidinyl)-imino]), bis(2,2,6,6-tetramethyl-4-piperidinyl)sebacate, bis(1,2,2,6,6-pentamethyl-4-piperidinyl)sebacate, bis(1-octyloxy-2,2,6,6-tetramethyl-4-piperidinyl)sebacate, bis(1,2,2,6,6-pentamethyl-4-piperidinyl)[3,5bis(1,1-dimethylethyl-4-hydroxy-phenyl) methyl]butyl propanedioate, 8-acetyl-3-dodecyl-7,7,9,9,-tetramethyl-1,3,8-triazaspiro(4,5)decane-2,4-dion, dodecyl/tetradecyl-3-(2,2,4,4-tetramethyl-2I-oxo-7-oxa-3,20-diazal dispiro(5.1.11.2)henicosan-20-yl)propionate.

To form a coating composition that has a high level of weatherability and resistance to UV degradation, a combination of above described ultraviolet light absorbers, antioxidants and hindered amine light stabilizers can be used.

Typically, the composition is a solvent based composition and any of the known organic solvents may be used to form the coating composition. Typical solvents include aromatic hydrocarbons, such as, toluene, xylene; ketones, such as, acetone, methyl ethyl ketone, methyl isobutyl ketone, methyl amyl ketone and diisobutyl ketone; esters, such as, ethyl acetate, n-butyl acetate, isobutyl acetate; and mixtures of any of the above.

The novel coating composition may also include other conventional formulation additives, such as, wetting agents, leveling and flow control agents, for example, Resiflow®S (polybutylacrylate), BYK® 320 and 325 (high molecular weight polyacrylates), BYK® 347 (polyether-modified siloxane), rheology control agents, such as, fumed silica, defoamers, surfactants and emulsifiers to help stabilize the composition. Other additives that tend to improve mar resistance can be added, such as, silsesquioxanes and other silicate-based micro-particles.

The coating composition of this invention can be used as a clear coat that is applied over a pigmented base coat that may be a pigmented version of the composition of this invention or another type of a pigmented base coat. The clear coating can be in solution or in dispersion form.

Typically, a clear coating is then applied over the base coating before the base coating is fully cured, a so called "wet-on-wet process", and the base coating and clear coating are then fully cured at ambient temperatures or can be cured by heating to elevated temperatures of 40° C. to 100° C. for 15 to 45 minutes or from 40° C. to 170° C. for 15 to 45 minutes for those coating of this invention not susceptible to thermoreversible crosslinking. If used in refinishing vehicles, the base coat may be allowed to "dry to the touch" at ambient temperature conditions or under warm air before the clear coating is applied. The base coating and clear coating preferably have a dry coating thickness ranging from 25 to 75 microns and 25 to 100 microns, respectively. Also, the composition can be used as a matte clear coating composition that is typically applied to the interior of automobiles and trucks.

The novel coating composition may be used as a base coat or as a pigmented monocoat topcoat. Both of these compositions require the presence of pigments. Typically, a pigment-to-binder ratio of 0.1/100 to 200/100 is used depending on the color and type of pigment used. The pigments are formulated into mill bases by conventional procedures, such as, grinding, sand milling, and high speed mixing. Generally, the mill base comprises pigment and a binder or a dispersant or both in a solventborne or aqueous medium. The mill base is added in an appropriate amount to the coating composition with mixing to form a pigmented coating composition.

Any of the conventionally-used organic and inorganic pigments, such as, white pigments, like, titanium dioxide, color pigments, metallic flakes, such as, aluminum flake, special effects pigments, such as, coated mica flakes, coated aluminum flakes and the like and extender pigments can be used. It may be desirable to add flow control additives.

The novel coating composition may be used as a primer or a sealer in which case typical pigments used in primers would be added, such as, carbon black, barytes, silica, iron oxide and other pigments that are commonly used in primers in a pigment-to-binder ratio of 10/100 to 300/100. These primers and sealers exhibit exceptional adhesion to untreated bare metal substrates, such as, aluminum and steel substrates, and to treated metal substrates, such as galvanized steel, and provide excellent stone chip resistance.

The coating composition can be applied by conventional techniques, such as, spraying, electrostatic spraying, dipping, brushing, and flow coating.

The coating composition is particularly useful for the repair and refinish of automobile bodies and truck bodies and parts as a clear coat, pigmented base coat, mono-coat as a primer, sealer or primer surfacer.

The novel composition has also uses as binder for rapid cure chip coats. The novel composition of this invention can be combined with the isocyanate reagents described above directly without the use of a solvent or additional components and applied to an automobile body directly using application methods known in the art such as integrated multi-component applicators, spray guns or similar devices. Optionally, the combination of the composition of this invention including the typical isocyanate component under simple agitation forms a mass with a desired viscosity profile for direct application to a surface, e.g., a putty, using spatulas or other manual application devices, such as a squeegee.

The novel composition has uses for coating any and all items manufactured and painted by automobile sub-suppliers, frame rails, commercial trucks and truck bodies, including but not limited to beverage bottles, utility bodies, ready mix concrete delivery vehicle bodies, waste hauling vehicle bodies, and fire and emergency vehicle bodies, as well as any potential attachments or components to such truck bodies, buses, farm and construction equipment, truck caps and covers, commercial trailers, consumer trailers, recreational vehicles, including but not limited to, motor homes, campers, conversion vans, vans, large commercial aircraft and small pleasure aircraft, pleasure vehicles, such as, snow mobiles, all terrain vehicles, personal watercraft, motorcycles, and boats. The novel composition also can be used as a coating for industrial and commercial new construction and maintenance thereof; cement and wood floors; walls of commercial and residential structures, such as, office buildings and homes; amusement park equipment; concrete surfaces, such as parking lots and drive ways; asphalt and concrete road surface, wood substrates, marine surfaces; outdoor structures, such as bridges, towers; coil coating; railroad cars; printed circuit boards; machinery; OEM tools; signs; fiberglass structures; sporting goods; and sporting equipment.

The following are testing procedures used in the Examples:

Cotton Tack Free Time

Allow coated panel to dry for set period of time (e.g. 30 minutes). Drop a cotton ball from a height of 1 inch onto the surface of the panel and leave the cotton ball on the surface for a set time interval and invert panel. Repeat above until the time the cotton ball drops off the panel on inversion and note that as the cotton tack free time.

MEK Rubs

A coated panel is rubbed (100 times) with an MEK (methyl ethyl ketone) soaked cloth using a rubbing machine and any excess MEK is wiped off. The panel is rated from 1–10. Rating 10—no visible damage to the coating, rating 9—1–3 distinct scratches, rating 8—4–6 distinct scratches, rating 7—7–10 distinct scratches, rating 6—10–15 distinct scratches with slight pitting or slight loss of color, rating 5—15–20 distinct scratches with slight to moderate pitting or moderate loss of color, rating 4—scratches start to blend into one another, rating 3—only a few undamaged areas between blended scratches, rating 2—no visible signs of undamaged paint, rating 1 complete failure—bare spots are shown. The final rating is obtained by multiplying the number of rubs by the rating.

Water Spot Test

Water spot rating is a measure of how well the film is crosslinked early in the curing of the film. If water spot damage is formed on the film, this is an indication that the cure is not complete and further curing of the film is needed before the film can be wet sanded or buffed or moved from the spray both. The water spot rating is determined in the following manner.

Coated panels are laid on a flat surface and deionized water was applied with a pipette at 1 hour-timed intervals. A drop about ½ inch in diameter was placed on the panel and allowed to evaporate. The spot on the panel was checked for deformation and discoloration. The panel was wiped lightly with cheesecloth wetted with deionized water, which was followed by lightly wiping the panel dry with the cloth. The panel was then rated on a scale of 1 to 10. Rating of 10 best—no evidence of spotting or distortion of discoloration, rating 9—barely detectable, rating 8—slight ring, rating 7—very slight discoloration or slight distortion, rating 6—slight loss of gloss or slight discoloration, rating 5—definite loss of gloss or discoloration, rating of 4—slight etching or definite distortion, rating of 3—light lifting, bad etching or discoloration, rating of 2—definite lifting and rating of 1—dissolving of the film.

BK Dry Time

Surface drying times of coated panels measured according to ASTM D5895.

Swell Ratio

The swell ratio of a free film. (removed from a sheet of TPO—thermoplastic olefin) was determined by swelling the film in methylene chloride. The free film was placed between two layers of aluminum foil and using a LADD punch, a disc of about 3.5 mm in diameter was punched out of the film and the foil was removed from the film. The diameter of the unswollen film ($D_o$) was measured using a microscope with a 10× magnification and a filar lens. Four drops of methylene chloride were added to the film and the film was allowed to swell for a few second and then a glass slide was placed over the film and the swollen film diameter ($D_s$) was measured. The swell ratio was then calculated as follow:

$$\text{Swell Ratio} = (D_s)^2/(D_o)^2$$

Persoz Hardness Test

The change in film hardness of the coating was measured with respect to time by using a Persoz hardness tester Model No. 5854 (ASTM D4366), supplied by Byk-Mallinckrodt, Wallingford, Conn. The number of oscillations (referred to as Persoz number) were recorded.

Hardness (Fischer)

Hardness was measured using a Fischerscope® hardness tester (the measurement is in Newtons per square millimeter).

Gel Fraction

Measured according to the procedure set forth in U.S. Pat. No. 6,221,494 col. 8 line 56 to col. 9 line 2 which procedure is hereby incorporated by reference.

Direct to Metal Adhesion Test

Adhesion of a coating to bare metal substrates was determined according to ASTM D3359-02, the standard test method for measuring adhesion by tape test.

Time to Gel

The time in minutes it takes for a liquid coating to gel.

Infra Red Film Cure

The infra Red spectrum was taken of the films made from certain coating examples. The spectra were taken on films cured for 10 days at ambient room temperature conditions, after curing for 30 minutes at 140° C., and in some instances, after curing at ambient temperature conditions for 10 days followed by heating for 30 minutes at 140° C.

The present invention is further defined in the following Examples. It-should be understood that these Examples are given by way of illustration only. From the above discussion and these Examples, one skilled in the art can ascertain the essential characteristics of this invention, and without departing from the spirit and scope thereof, can make various changes and modifications of the invention to adapt it to various uses and conditions. As a result, the present invention is not limited by the illustrative examples set forth herein below, but rather is defined by the claims contained herein below.

In the following examples, all parts and percentages are on a weight basis unless otherwise indicated.

EXAMPLES

The following were used in the examples:

LC/MS (Liquid Chromatography/Mass Spectroscopy) analyses were performed on a Waters Alliance 2790 LC quipped with a MS (ES) interface. Column: Zorbax SB-C18, 2.1×150 mm at 50° C.; Solvents: A=99:1 water/acetonitrile, B=acetonitrile, C=methanol, D=80:20 acetonitrile/water; Conditions: 90% A/10% B/0.25% D to 0% A/100% B/0.25% D over 30 min, hold ten minutes, then return to initial conditions after 42 min; Wavelength: 191–799 nm; Flow rate: 0.25 mL/min.

$^1$H NMR and $^{13}$C NMR spectra were recorded on a Bruker Avance 400 spectrometer. $^1$H NMR and $^{13}$C NMR chemical shifts were referenced to residual $^1$H and $^{13}$C signals of the deuterated solvents.

General Preparation Procedure for Compounds (II)–(VII):

To a four-neck 2 L RBF (round bottom flask) fitted with an overhead stirrer, condenser and thermocouple was added under $N_2$ maleic anhydride (86.5 g, 0.84 mol), 500 mL toluene, and 1,6-hexanediol (50.0 g, 0.42 mol). The reaction mixture was then heated to 60° C. Within one hour, a white precipitate began to form, and the reaction was allowed to proceed overnight. The reaction mixture was then filtered through a coarse frit, and the resulting white solid was rinsed with little toluene and dried to constant weight. 129.8 g (99% yield) of the desired product, (Z)-2-Butenedioic-acid-1,6-hexanediyl-ester, was obtained ($^{13}$C NMR 125 MHz, DMSO-dimethyl sulfoxide): δ 166.4, 165.2, 131.2, 128.8, 64.4, 27.7, 25.0)

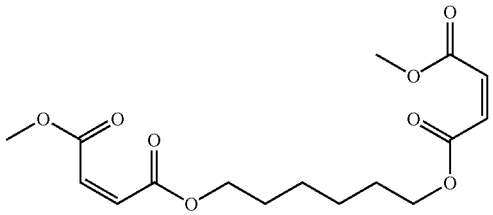

In the second step, this compound was transformed into the dimethylester following standard procedures such as reaction with MeI ($Me_2SO_4$)/$K_2CO_3$. To a four-neck 3 L RBF fitted with an overhead stirrer, addition funnel and thermocouple was added under $N_2$ (Z)-2-Butenedioic-acid-1,6-hexanediyl-ester (93.0 g, 0.30 mol) and 800 mL of DMF (dimethyl formamide). The mixture was stirred until the solid had dissolved before 98.2 g of $K_2CO_3$ (0.71 mmol, 2.4 eq.) was added. The reaction mixture was cooled in an ice bath to 0° C., and methyl iodide 44.2 mL (0.71 mol, 2.4 eq.) was added dropwise. The reaction mixture was stirred at room temperature overnight before it was filtered through a bed of celite. The DMF solvent was reduced by rotary evaporation, the residue was taken up in 1.5 L of ethyl acetate, washed with 4×1L 5% $KHSO_4$, 2×1L of half-saturated $NaHCO_3$, 2×1L of brine, dried over $MgSO_4$, filtered and concentrated. The residual brown oil was purified by chromatography on 600 g silica gel packed with 25% ethyl acetate in hexane. The dimethyl ester ($R_f$=0.28) was obtained in 31% yield as a pale yellow oil. ($^{13}$C NMR (125 MHz, CDCl$_3$=chloroform-d): δ 165.7, 165.2, 130.0, 129.5, 65.2, 52.1, 28.3, 25.5).

Diamines (II–VII) were then synthesized from the dimethyl ester by reaction in acetonitrile with excess amine at 50° C. For example, diamine (II) was synthesized in quantitative yield according to LC/MS (Liquid Chromatograph/Mass Spectoscopy) from 1.3 g (3.8 mmol) dimethyl ester and 1.54 mL (4 eq.) cyclohexylamine in 2 mL of acetonitrile after 16 h at 50° C., followed by solvent removal and removal of excess amine in vacuo.

Diamine (III) was synthesized in an analogous fashion from the dimethyl ester and secButyl amine, diamine (IV) from the dimethyl ester and nButyl amine, diamine (V) from the dimethyl ester and isoButyl amine, diamine (VI) from the dimethyl ester and neopentyl amine, diamine (VII) from the dimethyl ester and tertButyl amine.

General Preparation Procedure for Compounds (VIII)–(XIV):

To a four-neck 2 L round bottom flask fitted with an overhead stirrer, condenser and thermocouple was added under $N_2$ 1,4-cyclohexane dimethanol (110.0 g, 0.76 mol), 600 mL acetonitrile, and maleic anhydride (196.8 g, 1.91 mol). The reaction mixture was then heated to 50° C., and the reaction was allowed to proceed for three days. A large amount of a white precipitate had formed. The reaction mixture was filtered hot through a coarse frit, and the residue was washed with some acetonitrile. The white solid was dried under $N_2$ to constant weight, and 161.5 g (62% yield) of the desired product, (Z)-2-Butenedioic-acid-1,4-cyclohexanediylbis(methylene) ester, was obtained as characterized by LC/MS analysis. The overall yield was improved 80% by subsequent crystallizations from the mother liquor.

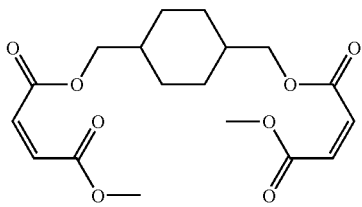

In the second step, this compound was transformed into the dimethylester following standard procedures such as reaction with MeI ($Me_2SO_4$)/$K_2CO_3$. To a four-neck 1 L RBF fitted with stir bar, addition funnel and thermocouple was added under $N_2$ (Z)-2-Butenedioic-acid-1,4-cyclohexanediylbis(methylene) ester (27.4 g, 0.08 mol) and 200 mL of DMF. The mixture was stirred until the solid had dissolved before 26.7 g of $K_2CO_3$ (0.19 mmol, 2.4 eq.) was added. The reaction mixture was cooled in an ice bath to 0° C., and methyl iodide (12 mL, 0.19 mol, 2.4 eq.) was added dropwise. The reaction mixture was stirred at room temperature overnight before it was filtered through a bed of celite. The DMF solvent was reduced by rotary evaporation, the residue was taken up in 1 L of ethyl acetate and washed with 2×150 mL 5% $KHSO_4$. After back-extraction using 2×500 mL ethyl acetate, the organic layers were combined, washed with 3×500 mL DI water, 2×150 mL of 5% $NaHCO_3$, 2×150 mL of brine, dried over $MgSO_4$, filtered and concentrated. The residual yellow solid was purified by recrystallization from ethyl acetate/hexane, yielding 14.0 g of the dimethyl ester as white solid (47% yield) in >98% purity according to LC/MS. ($^{13}C$ NMR (125 MHz, $CDCl_3$): δ 165.7, 165.2, 129.8, 129.7, 70.2, 52.1, 36.9, 28.8).

Diamines (VIII–XIV) were then synthesized from the dimethyl ester by reaction in acetonitrile with excess amine at 50° C. For example, diamine (IX) was synthesized in quantitative yield according to LC/MS from 1.3 g (3.8 mmol) dimethyl ester and 1.54 mL (4 eq.) secbutylamine in 2 mL of acetonitrile after 16 h at 50° C., followed by solvent removal and removal of excess amine in vacuo. Diamine (VIII) was synthesized in an analogous fashion from the dimethyl ester and cyclohexyl amine, diamine (X) from the dimethyl ester and nButyl amine, diamine (XI) from the dimethyl ester and isobutyl amine, diamine (XII) from the dimethyl ester and neopentyl amine, diamine (XIII) from the dimethyl ester and tertbutyl amine, and diamine (XIV) from the dimethyl ester and (2-methylbicyclo[2.2.1]heptan-2-yl)methanamine.

General Preparation Procedure for Compounds (XV)–(XIX) and (XXVII):

To a four-neck 2 L round bottom flask fitted with an overhead stirrer, condenser thermocouple, and two addition funnels was added under $N_2$ 1,4-cyclohexanedimethanol (35.4 g, 0.24 mol) and 1000 mL dry THF (tetrahydrofuran). Then $PPh_3$ (triphenylphosphine) (127.3 g, 0.49 mol) was added. The reaction mixture was cooled to −10° C., followed by slow addition of diisopropylazodicarboxylate (DIAD, 95%, 103.3 g, 0.49 mol). The solution became very viscous and eventually precipitated a yellow solid, then it was allowed to warm up to room temperature where it was stirred for about 10 minutes. The reaction mixture was cooled again to −10° C., followed by dropwise addition of monobutyl maleate (83.5 g, 0.49 mol), causing the yellow solid to dissolve again. The resulting orange solution was allowed to warm up to room temperature and stirred overnight. After work-up, the crude reaction product was chromatographed on silica (25% ethyl acetate/hexanes) ($R_f$=0.47), yielding 58.4 g of the desired bis-maleate as a pale yellow oil, which will eventually solidify (53% yield). ($^{13}C$ NMR (125 MHz, $CDCl_3$): δ 165.33, 165.30, 129.9 129.6, 70.1, 68.0, 65.2, 36.9, 34.4, 30.5, 28.8, 25.3, 19.1, 13.7).

Diamines (XV–XIX and XXVII) were then synthesized from the dibutyl ester by reaction in acetonitrile with excess amine at 50° C. For example, diamine (XVI) was synthesized in quantitative yield according to LC/MS from 1.23 g (2.7 mmol) dibutyl ester and 0.93 mL (3 eq.) sec-Butylamine in 1.5 mL of acetonitrile after 17 h at 50° C., followed by solvent removal and removal of excess amine in vacuo. Diamine (XV) was synthesized in an analogous fashion from the dibutyl ester and cyclohexyl amine, diamine (XVII) from the dibutyl ester and nButyl amine, diamine (XVIII) from the dibutyl ester and isoButyl amine, diamine (XIX) from the dibutyl ester and neopentyl amine, and diamine (XXVII) from the dibutyl ester and (2-methylbicyclo[2.2.1]heptan-2-yl)methanamine.

General Preparation Procedure for Compounds (XX)–(XXVI):

To a four-neck 2 L round bottom flask fitted with an overhead stirrer, condenser thermocouple, and two addition funnels was added under $N_2$ 1,4-cyclohexanedimethanol (34.8 g, 0.24 mol) and 650 mL dry THF. Then $PPh_3$ (126.6 g, 0.48 mol) was added. The reaction mixture was cooled to −10° C., followed by slow addition of diisopropylazodicarboxylate (DIAD, 95%, 102.7 g, 0.48 mol). The solution was allowed to warm up to room temperature where it was stirred for about 10 minutes. The reaction mixture was cooled again to −10° C., followed by dropwise addition of monocyclohexyl maleate (95.6 g, 0.48 mol) in 400 mL of dry THF, causing a yellow precipitate that had formed during the DIAD addition to dissolve again. The resulting orange solution was allowed to warm up to room temperature and stirred for three days. The solvent was removed by rotary evaporation leaving 390.1 g of brown oil behind that was triturated with 600 mL of diethyl ether. After filtration, diethyl ether was removed by rotary evaporation to yield 164 g of a pink solid that was subsequently chromatographed on silica (25% ethyl acetate/hexanes) ($R_f$=0.54), yielding 54.0 g of the desired bis-maleate as a white (44% yield). ($^{13}C$ NMR (125 MHz, $CDCl_3$): δ 165.3, 164.7, 130.5, 129.2, 73.9, 70.1, 67.9, 36.9, 34.4, 31.5, 28.8, 25.3, 23.8).

Diamines (XX–XXVI) were then synthesized from the dicyclohexyl ester by reaction in acetonitrile with excess amine at 50° C. For example, diamine (XXI) was synthesized in quantitative yield according to LC/MS from 31.5 g (0.06 mol) dicyclohexyl ester and 27.4 g (0.38 mol, 6 eq.) sec-Butylamine in 210 mL of dry acetonitrile after four days at 50° C., followed by solvent removal and removal of excess amine in vacuo. After filtration of the light hazy pale yellow oil, 38.0 g of diamine product were obtained in >96% purity according to LC/MS analysis (94% yield). Diamine (XX) was synthesized in an analogous fashion from the dicyclohexyl ester and cyclohexyl amine, diamine (XXII) from the dicyclohexyl ester and nButyl amine, diamine (XXIII) from the dicyclohexyl ester and isoButyl amine, diamine (XXIV) from the dicyclohexyl ester and nopentyl amine, diamine (XXV) from the dicyclohexyl ester and tertButyl amine, and diamine (XXVI) from the dicyclohexyl ester and (2-methylbicyclo[2.2.1]heptan-2-yl)methanamine.

General Preparation Procedure for Compounds (XXVIII)–(XLIII):

To a four-neck 250 mL RBF fitted with stirbar, condenser and thermocouple was added under $N_2$ DYTEK® amine (2-methylpentane-1,5-diamine) (10 g, 0.08 mol) and 10 mL dry acetonitrile, followed by maleic anhydride (17.5 g, 0.17 mol), resulting in an exothermic reaction and formation of a large amount of white solid. The reaction mixture was stirred for three hours, before the white solid was filtered off, washed with acetonitrile and dried to constant weight. 22.4 g product (84% yield) was obtained as a mixture of the bis-maleamic acid and the mono-maleamic-acid-mono-maleimide according to LC/MS analysis. ($^{13}C$ NMR (125 MHz, $CDCl_3$): δ 165.5, 165.4, 165.3, 132.9, 132.8, 131.80, 131.78, 45.0, 32.2, 31.0, 25.7, 17.5).

To a three-neck 100 mL RBF fitted with stirbar, addition funnel and thermocouple was added under $N_2$ DYTEK® bis-maleamic acid (5 g, 0.012 mol) and 20 mL of methanol. To this white slurry was added dropwise 38 mL of 1.25 M HCl in methanol. Most of the solid dissolved during the addition and eventually all was dissolved. After two hours, the solvent was removed by rotary evaporation, yielding 6.2 g of yellow oil. The crude oil was taken up in 50 mL of $CH_2Cl_2$, extracted with sodium bicarbonate solution, back-extracted into $CH_2Cl_2$, dried over magnesium sulfate and filtered. The solvent was removed by rotary evaporation, yielding 4.9 g of a pale yellow oil in >94% purity according to LC/MS as mixture of the bis-ester and mono-ester-mono-imide.

Diamines (XXVIII)–(XXXIII) were then synthesized from the bis-maleamic ester by reaction in acetonitrile with excess amine at 50° C. For example, diamine (XXIX) was synthesized from 62.9 g (0.19 mol) bis-maleamic ester and 57 mL (3 eq.) sec-Butylamine in 300 mL of dry acetonitrile after 2 days at 50° C., followed by solvent removal and removal of excess amine in vacuo. The resulting brown oil was then purified by chromatography on silica (50% ethyl acetate/hexanes), yielding 47.5 g of a diamine product mixture as a yellow oil (53% yield). Diamine (XXVIII) was synthesized in an analogous fashion from the the bis-maleamic ester and Cyclohexyl amine, diamine (XXX) from the the bis-maleamic ester and nButyl amine, diamine (XXXI) from the bis-maleamic ester and isoButyl amine, diamine (XXXII) from the bis-maleamic ester and Neopentyl amine, and diamine (XXXIII) from the bis-maleamic ester and tertButyl amine, Diamines (XXXIV)–(XXXV) were synthesized in an analogous reaction started from the DYTEK® bis-maleamic acid: to a three-neck 100 mL RBF fitted with stirbar, addition funnel and thermocouple was added under $N_2$ DYTEK® bis-maleamic acid and 20 mL of ethanol (XXXIV) or isopropanol (XXXV). To this white slurry was added dropwise 38 mL of 1.25 M HCl in ethanol (XXXIV) or isopropanol (XXXV). Most of the solid dissolved during the addition and eventually all was dissolved. After two hours, the solvent was removed by rotary evaporation, yielding a yellow oil. The crude oil was taken up in 50 mL of $CH_2Cl_2$, extracted with sodium bicarbonate solution, back-extracted into $CH_2Cl_2$, dried over magnesium sulfate and filtered. The solvent was removed by rotary evaporation, yielding in both cases a pale yellow oil in as mixture of the bis-ester and mono-ester-mono-imide.

Diamines (XXXIV)–(XXXV) were then synthesized from the bis-maleamic ester (ethyl-ester for XXXIV, isopropyl-ester for XXXV) by reaction in acetonitrile with excess sec-butyl amine at 50° C. as described above.

Diamines (XXXVI–XXXIX) were synthesized following an analogous procedure starting from 2,2-dimethyl-1,3-propanediamine, which was first converted into the bis-maleamic acid by reaction with maleic anhydride in acetonitrile. Subsequent methylation of the carboxylic ester functional groups with HCl/MeOH led to the formation of the bis-maleate, which was then treated with primary amine. Diamine (XXXVI) was synthesized from the bis-maleamic ester and secButyl amine, diamine (XXXVII) from the bis-maleamic ester and neopentyl amine, diamine (XXXVIII) from the bis-maleamic ester and cyclohexyl amine, and diamine (XXXIX) from the the bis-maleamic ester and tertButyl amine.

Finally, diamines (XL–XLIII) were synthesized following an analogous procedure starting from (4-(aminomethyl)cyclohexyl)methanamine (XL) and Jeffamine HK511 (XLI–XLIII), the latter being a mixture of isomers.

General Preparation Procedure for Compound (XLIX):

L,L-Leucine 1,4-cyclohexane dimethanol diester

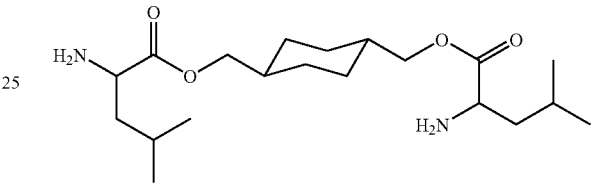

L-leucine (22.73 g, 264 mmol), 1,4-cyclohexanedimethanol (17.58 g, 120 mmol) and p-toluenesulfonic acid monohydrate (57.08 g, 300 mmol) were added to a three-neck RBF and 100 ml toluene was added to the mixture. A Dean-Stark trap with a reflux condenser was then attached to the flask with the receiving side filled to overflow point with toluene under nitrogen. The temperature was increased to 150° C. and the mixture was refluxed for 24 h. The reaction mixture was cooled to room temperature and more L-leucine (8.26 g, 96 mmol) and p-toluenesulfonic acid monohydrate (19.04 g, 100 mmol) was added to it, followed by refluxing for another 6 h to drive the reaction to completion. After cooling the reaction to room temperature, the toluene solvent was removed under vacuum and careful neutralization of the residue was carried out using aqueous sodium bicarbonate solution at 60° C. The mixture was then extracted with dichloromethane (3×200 ml), the combined organic layers were dried over sodium sulfate, and the solvent was removed to give a quantitative yield of the product, which was used without further purification.

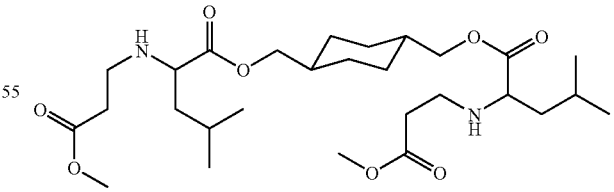

To L,L-Leucine 1,4-cyclohexanedimethanol diester (3.7 g, 10 mmol) and triethyl amine (2.8 ml, 20 mmol) at room temperature was added methyl acrylate (1.29 g, 15 mmol) and the resulting mixture was stirred at 80° C. for 1 day, after which more triethyl amine (2.8 ml, 20 mmol) and methyl acrylate (1.29 g, 15 mmol) was added, and the reaction was stirred for two more 2 days. Removal of volatile material under vacuum followed by chromatography on silica using 1:1 ethyl acetate-hexane mixture with 5–10% acetone gave 4.3 g (79%) of the desired adduct (XLIX).

General Preparation Procedure for Compound (LI)

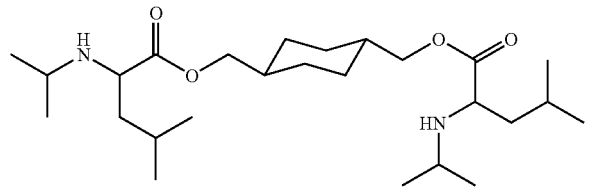

To L,L-Leucine 1,4-cyclohexanedimethanol diester (3.7 g, 10 mmol) in 15 ml methanol was added while stirring at room temperature first acetone (3.48 g, 60 mmol) and then 100 ml 1M sodium cyanoborohydride in THF, and the resulting mixture was allowed to stir at 60° C. for 3 days. After cooling to room temperature the reaction mixture was concentrated under vacuum, taken up in dichloromethane (100 ml) and washed with water (100 ml). The organic layer was dried over MgSO$_4$, concentrated under vacuum and purified by chromatography over silica using 1:1 ethyl acetate-hexane mixture with 2–5% acetone yielding 3.2 g (71%) of the desired product (LI).

General Preparation Procedure for Compound (LIII):

L-(4-(hydroxymethyl)cyclohexyl)methyl 2-amino-4-methylpentanoate

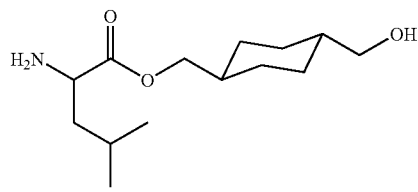

L-leucine (8.61 g, 100 mmol), 1,4-cyclohexanedimethanol (18.1 g, 120 mmol) and p-toluenesulfonic acid monohydrate (28.56 g, 150 mmol) were taken in a three neck round bottom flask and 100 ml toluene was added to the mixture. Dean-stark trap with a reflux condenser was then attached to the flask with the receiving side filled to overflow point with toluene under nitrogen. Temperature was increased to 150° C. and the mixture refluxed for 24 h. After cooling the reaction to room temperature toluene was removed under vacuum and careful neutralization of the residue was carried out using aqueous sodium bicarbonate solution. The mixture was then extracted with dichloromethane (3×200 ml), the combined organic layers were dried over sodium sulfate, and the solvent was removed to give a mixture of mono and diester products and predominantly mono-ester. The reaction mixture was used without further purification.

(4-(hydroxymethyl)cyclohexyl)methyl 2-(2-(methoxycarbonyl)ethylamino)-4-methyl pentanoate

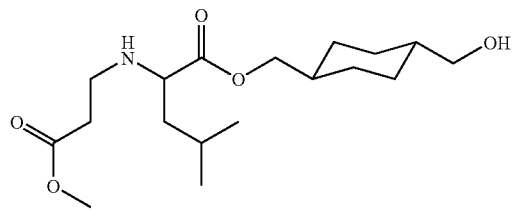

To the crude mixture containing predominantly L-(4-(hydroxymethyl)cyclohexyl) methyl 2-amino-4-methylpentanoate (2.57 g, 10 mmol) was added triethyl amine (2.8 ml, 20 mmol) and methyl acrylate (1.29 g, 15 mmol) at room temperature and the resulting mixture was stirred at 80° C. for 2days. Removal of volatile material under vacuum followed by chromatography over silica using 1:1 ethyl acetate-hexane mixture with 2–5% acetone gave 1.58 g (46%) of the desired product.

General Peparation Procedure for Compound (LVII):

3-(sec-butylcarbamoyl)acrylic acid

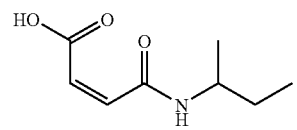

To a stirred solution of maleic anhydride, 95% (42.1 g, 0.4 mol) in 500 mL diethyl ether at 0° C. was added drop wise sec-butyl amine (29.25 g, 0.4 mol) in 50 mL diethyl ether. The resulting mixture was stirred while a solid formed, which was recovered by filtration. The residue was washed with 2×100 mL diethyl ether and dried to yield 51.76 g of the desired compound.

Methyl 3-(sec-butylcarbamoyl)acrylate

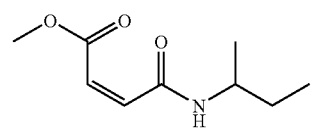

To 3-(sec butylcarbamoyl)acrylic acid (20 g, 117 mmol) at room temperature was added 150 mL 1.2M HCl in methanol. The resulting mixture was stirred for two hours. Solvents were removed in vacuo to give the desired ester, which was used without further purification.

Methyl 3-(sec-butylcarbamoyl)-2-(6-hydroxyhexylamino) propanoate

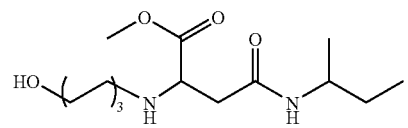

To methyl 3-(sec-butylcarbamoyl)acrylate from the above reaction at room temperature was added the 6-amino-1-hexanol (13.7 g, 117 mmol) and the resulting mixture was stirred overnight to give the desired product.

General Preparation Procedure for Compound (LXVI):

A solution of fumaroyl chloride in 300 mL of anhydrous THF was added under nitrogen and at 0° C. slowly over a one-hour period to a solution of 1,4-Cyclohexanedimethanol in 300 mL of anhydrous THF, using a 5:1 molar excess of the diol. (Note: The diol has to be used in excess, otherwise one sees over-addition of the fumaroyl chloride). After the addition was completed, the solution was kept at 0° C. for one hour and afterwards was allowed to stir at room temperature overnight.

Excess diol was difficult to remove from the reaction product during the aqueous work-up. Therefore the reaction mixture as such was subsequently treated with secbutyl amine (slight excess with respect to the original amount of fumaroyl chloride). The amine-diol product in the product mixture with 1,4-Cyclohexanedimethanol was identified by LC/MS.

EXAMPLE 1

Preparation of the Clearcoat Composition

TABLE 1

| Coating Composition | 1A | 1B | 1C | |
|---|---|---|---|---|
| Portion 1 | | | | |
| NCO Reactive Comp. XX (80% in butyl acetate) | 43.57 | — | — | |
| NCO Reactive Comp. IX | — | 25.49 | — | |
| NCO Reactive Comp. XI | — | — | 25.49 | |
| Butyl Acetate | 14.03 | 18.8 | 18.8 | |
| Flow Additive* | 0.54 | 0.47 | 0.47 | |
| Portion 2 | | | | |
| Tolonate ® HDT** | 19.47 | 19.47 | 19.47 | |
| Coating Composition | 1D | 1E | 1F | 1G |
| Portion 1 | | | | |
| NCO Reactive Comp. XVI | 29.7 | — | — | — |
| NCO Reactive Comp. XXI | — | 32.28 | — | — |
| NCO Reactive Comp. XXIX (80% in butyl acetate) | — | — | 30.16 | — |
| NCO Reactive Comp. XXXI | — | — | — | 26.91 |
| Butyl acetate | 20.58 | 21.66 | 12.22 | 19.28 |
| Flow additive (described above) | 0.49 | 0.52 | 0.43 | 0.46 |
| Portion 2 | | | | |
| Tolonate ® HDT (described above) | 19.47 | 19.47 | 19.47 | 19.47 |

*20% BYK 301 ® flow additive, supplied by BYK-CHEMIE in propylene glycol monomethyl ether.
**Tolonate ® HDT isocyanate trimer of hexamethylene diisocyanate supplied by Rhodia Inc.

In the preparation of each of the above coating compositions 1A–1G, Portion 1 was charged into a mixing vessel in the order shown above and mixed and then Portion 2 was charged into the mixing vessel and thoroughly mixed with Portion 1. The calculated weight solids of each of the above compositions was 70%. Each of the above prepared coating compositions 1A–1G was applied with a doctor blade over a separate phosphated cold roll steel panel primed with a layer of PowerCron® Primer supplied by PPG, Pittsburgh, Pa., to a dry coating thickness of about 50 micrometers and air dried at ambient temperature conditions. With Coating Compositions 1B, 1C, 1F, 1G a second set of panels were prepared and cured for 30 minutes at 140° C. Then the Panels were tested using the test set forth in the following table and the test results are shown in the table.

| | Ex. 1A | Ex. 1B | Ex. 1C | Ex. 1D | Ex. 1E | Ex. 1F | Ex. 1G |
|---|---|---|---|---|---|---|---|
| NCO Reactive Comp | XX | IX | XI | XVI | XXI | XXIX | XXXI |
| Theo. Eq. Wt. | 351.1 | 257 | 257 | 299 | 325 | 243.3 | 271.4 |
| Time to Gel (min) | 129 | 238 | 8 | NA | 201 | 15 | 40 |
| BK 3 time (min) | 37.8 | 82.7 | 23.6 | 113 | 115 | 16.5 | 40.2 |
| BK 4 time (min) | 111 | 111 | 44.9 | 220 | 276 | 47.2 | 56.7 |
| Cotton Tack Free time (min) | 69 | <103 | 90 | 185 | >240 | 50 | 20 |
| Water Spot- 4 hrs RT | 8 | 5 | 9 | 5 | 8.5 | 9 | 9 |
| MEK rubs 4 hrs RT | 600 | 500 | 500 | 400 | 400 | NA | NA |
| Swell Ratio 1 day RT | 2.21 | 2.74 | 2.07 | 2.43 | 2.68 | 1.92 | 2.38 |
| Swell Ratio 7 day RT | 2.19 | 2.49 | 2.06 | 2.29 | 2.44 | 1.75 | 2.15 |
| Swell Ratio 30 day RT | 2.24 | 2.26 | NA | 2.24 | 2.26 | 1.67 | 2.00 |
| Persoz Hardness 4 hrs RT | 139 | 93 | 53 | 204 | 190 | 38 | 30 |
| Fischer Hardness 1 day RT | 71.2 | 113.2 | 24.5 | 105 | 118 | 32 | 14.7 |
| Fischer Hardness 30 days RT | 116 | 135.5 | 125 | 109 | 129 | 128 | 104 |

-continued

|  | Ex. 1A | Ex. 1B | Ex. 1C | Ex. 1D | Ex. 1E | Ex. 1F | Ex. 1G |
|---|---|---|---|---|---|---|---|
| Gel Fraction 30 days RT | 93.39 | 96.20 | NA | 93.42 | 95.83 | 95.11 | 95.21 |
| Swell Ratio 30 min 140° C. | NA | Brittle, poor cure | Brittle, poor cure | NA | NA | 1.89 | 2.50 |
| Gel Fraction 30 min 140° C. | NA | Brittle, poor cure | Brittle, poor cure | NA | NA | 96.36 | 93.30 |
| Fischer Hardness 30 min 140° C. | NA | 20.9 | 152 | NA | NA | 171 | 127 |
| MEK Rubs 30 min 140° C. | NA | 10 | 100 | NA | NA | NA | NA |
| MEK Rubs 10 day RT | Na | 700 | 100 | NA | NA | NA | NA |
| MEK Rubs 10 day RT plus 30 min 140° C. | NA | 45 | 60 | NA | NA | NA | NA |
| Infra red film cure * 30 days RT | NA | Significant absorption | Significant absorption | NA | NA | Significant absorption | Significant absorption |
| 30 min 140° C. | NA | Significantly less absorption | Significantly less absorption | NA | NA | Significant absorption | Significant absorption |
| 30 days RT plus 30 min 140° C. | NA | Significantly less absorption | Significantly less absorption | NA | NA | Significant absorption | Significant absorption |

*Infra red film cure - urea peaks at 1625 cm-1 & 1530 cm-1
Theo. Eq. Wt. - theoretical equivalent weight
NA - not available
Rt - room temperature The above results show that coatings made from the isocyanate-reactive components of this invention have excellent early cure at room temperature conditions, as is evident from the short BK dry times, good to excellent early water spot, good to excellent MEK rubs, hardness at 4 hours, and good 1 day swell ratio. These coatings remain fluid for a useful period of time, and in some instances, such as, in examples 1A, 1B and 1E, for extended periods of time. The films also have excellent final properties, such as, hardness and gel fraction.

Some the coatings of this invention exhibit the ability to undergo thermo-reversible crosslinking, such as, examples 1B and 1C, while others do not, such as, examples 1F and 1G. The data in the table show that when coatings of examples 1B and 1C are heated above their Tg, for example, for 30 minutes at 140° C., they lose a significant amount of their crosslinking. This can be seen in the table as a loss of MEK resistance when the films are either cured initially at 140° C., or if films are cured for 10 days at room temperature followed by subsequently heating the films for 30 minutes at 140° C. (MEK rubs decrease from 700 to 45 in Example 1B and from 100 to 60 in Example 1C). Additional evidence of this thermo-reversible crosslinking can be seen using Infra Red Spectroscopy. The Infra red spectra of these films cured at room temperature show significant peaks at 1625 and 1530 cm-1, characteristic of the urea formed upon crosslinking of the novel amines of this invention with Isocyanate. When these films are subjected to temperatures of 140° C. for 30 minutes, a significant decrease in the height of the peaks at 1625 and 1530 cm-1 occurs, almost to a point of complete loss of these peaks in the Infra Red spectrum.

Other coatings of this invention, particularly shown in Examples 1F and 1G, do not undergo the thermo-reversible crosslinking. This can be seen in the table by looking at the film properties of these coatings when cured at room temperature and comparing this to the film properties after 140 C cure. The results are similar for swell ratios, gel fractions, hardness and Infra red cure.

EXAMPLE 2

(Direct-to-Metal Adhesion)

In the following Example, the reactive isocyanate compound XXXIV was combined with Desmodur® 3300 at 70% weight in butyl acetate in a 30 mm vial and vortexed for 20 seconds. The coating composition was applied with a doctor blade (5 mil film) over A) clean, unpolished aluminum, B) clean, unpolished cold roll steel, and C) clean, unpolished galvanized steel. The adhesion of the coating film was measured according to the aforementioned "X-hatch" tape test after 1 day, 3 days and seven days. The results are summarized in the attached table, showing excellent adhesion (10=highest rating) for cold roll steel and galvanized steel after one day, and excellent adhesion to aluminum after 3 days.

| Compound XXXIV | | | | | |
|---|---|---|---|---|---|
| Day 1 Plates | Tape used | Rating | Day 3 Plates | Rating | Day 7 Plates | Rating |
| A | 898 | 1 | A | 10 | A | 10 |
| B | 898 | 10 | B | 10 | B | 10 |
| C | 898 | 10 | C | 10 | C | 10 |
The invention claimed is:
1. A hydroxy amine compound having a structure selected from at least one of the following formulae (LV) to (LXV):
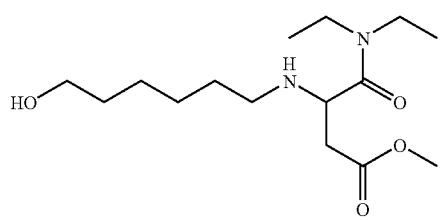
(LV)
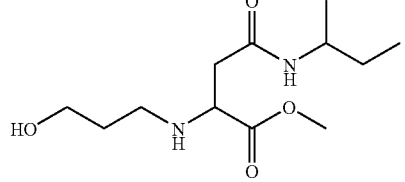
(LVI)
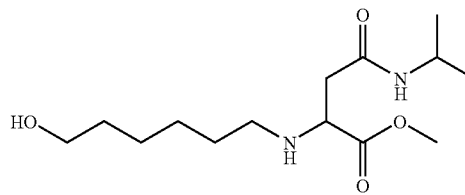
(LVII)
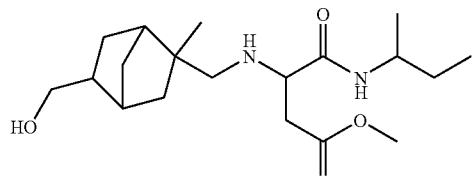
(LVIII)
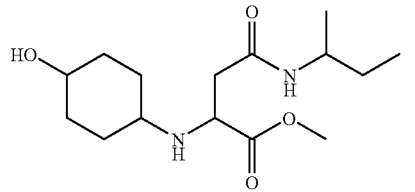
(LIX)
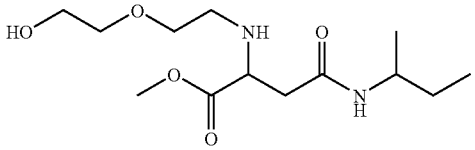
(LX)
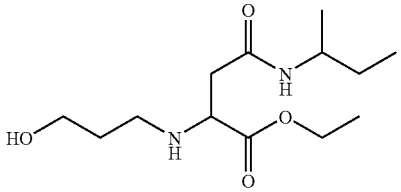
(LXI)
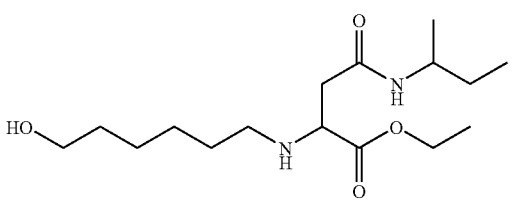
(LXII)
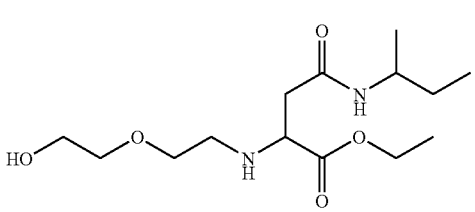
(LXIII)
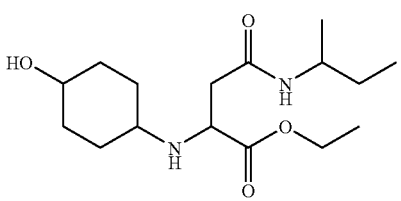
(LXIV)
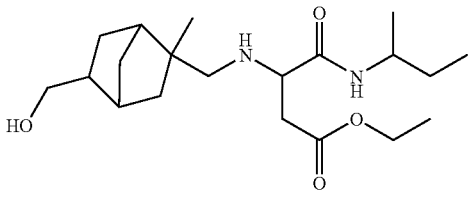
(LXV)
or isomers or isomeric mixtures thereof.
* * * * *